United States Patent
Snyder et al.

(10) Patent No.: US 11,305,095 B2
(45) Date of Patent: Apr. 19, 2022

(54) MICROFABRICATED CATHETER HAVING AN INTERMEDIATE PREFERRED BENDING SECTION

(71) Applicant: SCIENTIA VASCULAR, LLC, West Valley City, UT (US)

(72) Inventors: Edward J. Snyder, Park City, UT (US); John A. Lippert, Park City, UT (US); Todd H. Turnlund, Park City, UT (US); Clark C. Davis, Holladay, UT (US)

(73) Assignee: SCIENTIA VASCULAR, LLC, West Valley City, UT (US)

( * ) Notice: Subject to any disclaimer, the term of this patent is extended or adjusted under 35 U.S.C. 154(b) by 65 days.

(21) Appl. No.: 16/281,046

(22) Filed: Feb. 20, 2019

(65) Prior Publication Data

US 2019/0255290 A1    Aug. 22, 2019

Related U.S. Application Data

(60) Provisional application No. 62/633,939, filed on Feb. 22, 2018.

(51) Int. Cl.
*A61M 25/01*     (2006.01)
*A61M 25/00*     (2006.01)

(52) U.S. Cl.
CPC ...... *A61M 25/0138* (2013.01); *A61M 25/005* (2013.01); *A61M 25/0051* (2013.01);
(Continued)

(58) Field of Classification Search
CPC ............ A61M 25/0138; A61M 25/005; A61M 25/0051; A61M 25/0053; A61M 25/0054;
(Continued)

(56) References Cited

U.S. PATENT DOCUMENTS

| 2,022,065 A | 11/1935 | Wappler |
| 2,187,299 A | 1/1940 | Burkhardt |

(Continued)

FOREIGN PATENT DOCUMENTS

| AU | 723040 | 12/1997 |
| AU | 733966 | 5/2001 |

(Continued)

OTHER PUBLICATIONS

U.S. Appl. No. 15/606,607, Nov. 19, 2019, Final Office Action.
(Continued)

*Primary Examiner* — James D Ponton
(74) *Attorney, Agent, or Firm* — Workman Nydegger

(57) ABSTRACT

The present disclosure relates to devices and methods for accessing a targeted vessel, such as a coronary artery, near the aortic root. A catheter device includes a proximal section, an intermediate section, and a distal section. The intermediate section includes a more proximal section (a proximal-intermediate section) and a more distal section (a distal-intermediate section). The proximal-intermediate section is microfabricated to enable preferred bending along a single plane. The distal-intermediate section is more rigid than the proximal-intermediate section and the distal section. In use, the proximal-intermediate section abuts against the aortic wall and bends to allow the distal-intermediate section to extend across the aortic root toward a targeted vessel on the opposite side of the aorta.

20 Claims, 12 Drawing Sheets

(52) U.S. Cl.
CPC .... *A61M 25/0053* (2013.01); *A61M 25/0054* (2013.01); *A61M 25/0012* (2013.01); *A61M 25/0052* (2013.01); *A61M 25/0144* (2013.01); *A61M 2025/0188* (2013.01)

(58) Field of Classification Search
CPC .......... A61M 25/0012; A61M 25/0052; A61M 25/0144; A61M 2025/0188
See application file for complete search history.

(56) References Cited

U.S. PATENT DOCUMENTS

| | | | |
|---|---|---|---|
| 3,183,702 A | 5/1965 | Zittel | |
| 3,572,334 A | 3/1971 | Petterson | |
| 3,612,058 A | 10/1971 | Ackerman | |
| 3,709,271 A | 1/1973 | Flory | |
| 3,920,058 A | 11/1975 | Walker | |
| 4,163,406 A | 8/1979 | Crawford | |
| 4,239,069 A | 12/1980 | Zimmerman | |
| 4,416,312 A | 11/1983 | Ostberg | |
| 4,688,540 A | 8/1987 | Ono | |
| 4,719,924 A | 1/1988 | Crittenden | |
| 4,801,297 A * | 1/1989 | Mueller et al. | A61M 25/00 604/280 |
| 4,846,186 A | 7/1989 | Box | |
| 4,895,168 A | 1/1990 | Machek | |
| 4,989,608 A | 2/1991 | Ratner | |
| 5,047,045 A | 9/1991 | Arney et al. | |
| 5,069,217 A | 12/1991 | Fleischhacker | |
| 5,084,022 A | 1/1992 | Claude | |
| 5,095,915 A | 3/1992 | Angelson | |
| 5,102,390 A | 4/1992 | Crittenden et al. | |
| 5,147,317 A | 9/1992 | Shank | |
| 5,154,725 A | 10/1992 | Leopold | |
| 5,174,302 A | 12/1992 | Palmer | |
| 5,315,996 A | 5/1994 | Lundquist | |
| 5,326,374 A | 7/1994 | Ilbawi et al. | |
| 5,345,945 A | 9/1994 | Hodgson et al. | |
| 5,372,587 A | 12/1994 | Hammerslag | |
| 5,382,259 A | 1/1995 | Phelps | |
| 5,385,152 A | 1/1995 | Abele | |
| 5,437,288 A | 8/1995 | Schwartz | |
| 5,441,483 A | 8/1995 | Avitall | |
| 5,506,682 A | 4/1996 | Pryor | |
| 5,507,751 A | 4/1996 | Goode et al. | |
| 5,551,444 A | 9/1996 | Finlayson | |
| 5,554,114 A | 9/1996 | Wallace et al. | |
| 5,569,218 A * | 10/1996 | Berg | A61M 25/0009 138/134 |
| 5,573,520 A | 11/1996 | Schwartz | |
| 5,573,867 A | 11/1996 | Zafred et al. | |
| 5,659,205 A | 8/1997 | Weisser | |
| 5,673,707 A | 10/1997 | Chandrasekaran | |
| 5,676,659 A | 10/1997 | McGurk | |
| 5,685,568 A | 11/1997 | Pirrello | |
| 5,685,868 A | 11/1997 | Lundquist | |
| 5,690,120 A | 11/1997 | Jacobsen | |
| 5,706,826 A | 1/1998 | Schwager | |
| 5,741,429 A | 4/1998 | Donadio | |
| 5,746,701 A | 5/1998 | Noone | |
| 5,792,154 A | 8/1998 | Doan | |
| 5,800,454 A | 9/1998 | Jacobsen | |
| 5,833,631 A | 11/1998 | Nguyen | |
| 5,833,632 A | 11/1998 | Jacobsen | |
| 5,842,461 A | 12/1998 | Azuma | |
| 5,860,963 A | 1/1999 | Azam | |
| 5,876,356 A | 3/1999 | Viera et al. | |
| 5,911,715 A | 6/1999 | Berg | |
| 5,911,717 A | 6/1999 | Jacobsen | |
| 5,916,194 A | 6/1999 | Jacobsen | |
| 5,931,830 A | 8/1999 | Jacobsen | |
| 5,954,672 A | 9/1999 | Schwager | |
| 6,004,279 A | 12/1999 | Crowley | |
| 6,014,919 A | 1/2000 | Jacobsen | |
| 6,017,319 A | 1/2000 | Jacobsen | |
| 6,022,343 A | 2/2000 | Johnson et al. | |
| 6,022,369 A | 2/2000 | Jacobsen | |
| 6,027,863 A | 2/2000 | Donadis | |
| 6,033,288 A | 3/2000 | Weisshaus | |
| 6,033,394 A | 3/2000 | Vidlund | |
| 6,056,702 A | 5/2000 | Lorenzo | |
| 6,063,101 A | 5/2000 | Jacobsen | |
| 6,110,164 A | 8/2000 | Vidlund | |
| 6,132,389 A | 10/2000 | Cornish | |
| 6,139,511 A | 10/2000 | Huter | |
| 6,168,570 B1 | 1/2001 | Ferrera | |
| 6,179,828 B1 | 1/2001 | Mottola | |
| 6,183,410 B1 | 2/2001 | Jacobsen | |
| 6,183,420 B1 | 2/2001 | Douk et al. | |
| 6,214,042 B1 | 4/2001 | Jacobsen | |
| 6,228,073 B1 | 5/2001 | Noone | |
| 6,245,030 B1 | 6/2001 | Dubois | |
| 6,251,086 B1 | 6/2001 | Cornelius | |
| 6,260,458 B1 | 7/2001 | Jacobsen | |
| 6,261,246 B1 | 7/2001 | Pantages et al. | |
| 6,273,881 B1 * | 8/2001 | Kiemeneij | A61M 25/0041 604/532 |
| 6,302,870 B1 | 10/2001 | Jacobsen | |
| 6,306,105 B1 | 10/2001 | Rooney | |
| 6,346,091 B1 | 2/2002 | Jacobsen | |
| 6,356,791 B1 | 3/2002 | Westlund | |
| 6,402,706 B2 | 6/2002 | Richardson et al. | |
| 6,428,489 B1 | 8/2002 | Jacobsen | |
| 6,431,039 B1 | 8/2002 | Jacobsen | |
| 6,436,056 B1 | 8/2002 | Wang et al. | |
| 6,440,088 B1 | 8/2002 | Jacobsen | |
| 6,458,867 B1 | 10/2002 | Wang et al. | |
| 6,464,651 B1 | 10/2002 | Hiejima et al. | |
| 6,492,615 B1 | 12/2002 | Flanagan | |
| 6,494,894 B2 | 12/2002 | Mirarchi | |
| 6,527,732 B1 | 3/2003 | Strauss | |
| 6,527,746 B1 | 3/2003 | Oslund | |
| 6,553,880 B2 | 4/2003 | Jacobsen | |
| 6,554,820 B1 | 4/2003 | Wendlandt | |
| 6,558,355 B1 | 5/2003 | Metzger | |
| 6,579,246 B2 | 6/2003 | Jacobsen | |
| 6,602,207 B1 | 8/2003 | Mam | |
| 6,606,985 B2 | 8/2003 | Negishi | |
| 6,610,046 B1 | 8/2003 | Usami et al. | |
| 6,627,724 B2 | 9/2003 | Meijs et al. | |
| 6,652,508 B2 | 11/2003 | Griffin | |
| 6,671,560 B2 | 12/2003 | Westlund | |
| 6,766,720 B1 | 7/2004 | Jacobsen | |
| 6,805,676 B2 | 10/2004 | Klint | |
| RE39,018 E | 3/2006 | Azuma | |
| 7,024,885 B2 | 4/2006 | Villalobos | |
| 7,097,624 B2 | 8/2006 | Campion | |
| 7,110,910 B1 | 9/2006 | Deffenbaugh | |
| 7,128,718 B2 | 10/2006 | Hojeibane et al. | |
| 7,182,735 B2 | 2/2007 | Shireman | |
| 7,276,062 B2 | 10/2007 | McDaniel et al. | |
| 7,338,345 B2 | 3/2008 | Fujinami | |
| 7,421,929 B2 | 9/2008 | French | |
| 7,494,474 B2 | 2/2009 | Richardson et al. | |
| 7,507,246 B2 | 3/2009 | McGuckin et al. | |
| 7,621,880 B2 | 11/2009 | Ryan | |
| 7,637,875 B2 | 12/2009 | Itou | |
| 7,641,622 B2 | 1/2010 | Satou | |
| 7,670,302 B2 | 3/2010 | Griffin | |
| 7,699,792 B2 | 4/2010 | Hofmann | |
| 7,722,545 B2 | 5/2010 | Bertsch | |
| 7,722,552 B2 | 5/2010 | Aimi | |
| 7,744,545 B2 | 6/2010 | Aimi | |
| 7,747,314 B2 | 6/2010 | Parins | |
| 7,753,859 B2 | 7/2010 | Kinoshita | |
| 7,766,896 B2 | 8/2010 | Volk | |
| 7,769,839 B2 | 8/2010 | Boivie et al. | |
| 7,785,273 B2 | 8/2010 | Eskuri | |
| 7,789,839 B2 | 9/2010 | Lupton | |
| 7,806,837 B2 | 10/2010 | Rasmussen | |
| 7,878,984 B2 | 2/2011 | Davis | |
| 7,883,474 B1 | 2/2011 | Mirigian | |
| 7,914,467 B2 | 3/2011 | Layman et al. | |
| 7,942,832 B2 | 5/2011 | Kanuka | |

(56) References Cited

U.S. PATENT DOCUMENTS

| | | |
|---|---|---|
| 7,989,042 B2 | 8/2011 | Obara et al. |
| 8,043,314 B2 | 10/2011 | Noriega et al. |
| 8,048,004 B2 | 11/2011 | Davis et al. |
| 8,105,246 B2 | 1/2012 | Voeller |
| 8,128,579 B2 | 3/2012 | Chen |
| 8,128,580 B2 | 3/2012 | Fujimagari |
| 8,137,293 B2 | 3/2012 | Zhou |
| 8,167,821 B2 | 5/2012 | Sharrow et al. |
| 8,257,279 B2 | 9/2012 | Jacobsen |
| 8,292,828 B2 | 10/2012 | Uihlein |
| 8,357,140 B2 | 1/2013 | Majercak |
| 8,376,961 B2 | 2/2013 | Layman |
| 8,377,056 B2 | 2/2013 | Oyola et al. |
| 8,409,114 B2 | 4/2013 | Parins |
| 8,444,577 B2 | 5/2013 | Bunch |
| 8,454,535 B2 | 6/2013 | Majercak |
| 8,460,213 B2 | 6/2013 | Northrop |
| 8,468,919 B2 | 6/2013 | Christian |
| 8,500,658 B2 | 8/2013 | Boyle |
| 8,517,959 B2 | 8/2013 | Kurosawa |
| 8,535,243 B2 | 9/2013 | Shireman |
| 8,540,648 B2 | 9/2013 | Uihlein |
| 8,551,020 B2 | 10/2013 | Chen et al. |
| 8,551,021 B2 | 10/2013 | Voeller |
| 8,622,931 B2 | 1/2014 | Teague |
| 8,622,933 B2 | 1/2014 | Maki |
| 8,728,075 B2 | 5/2014 | Wu et al. |
| 8,758,269 B2 | 6/2014 | Miyata et al. |
| 8,795,202 B2 | 8/2014 | Northrop |
| 8,795,254 B2 | 8/2014 | Layman |
| 8,821,477 B2 | 9/2014 | Northrop |
| 8,870,790 B2 | 10/2014 | Jacobsen |
| 8,900,163 B2 | 12/2014 | Jacobsen |
| 8,915,865 B2 | 12/2014 | Jacobsen et al. |
| 8,932,235 B2 | 1/2015 | Jacobsen |
| 8,936,558 B2 | 1/2015 | Jacobsen |
| 8,939,916 B2 | 1/2015 | Jacobsen |
| 8,956,310 B2 | 2/2015 | Miyata |
| 9,067,332 B2 | 6/2015 | Lippert |
| 9,067,333 B2 | 6/2015 | Lippert |
| 9,072,873 B2 | 7/2015 | Lippert |
| 9,072,874 B2 | 7/2015 | Northrop |
| 9,364,589 B2 | 6/2016 | Cage |
| 9,550,013 B2 | 1/2017 | Kawasaki |
| 9,616,195 B2 | 4/2017 | Lippert |
| 9,623,212 B2 | 4/2017 | Tano |
| 9,662,798 B2 | 5/2017 | Christian |
| 9,700,702 B2 | 7/2017 | Tano |
| 9,848,882 B2 | 12/2017 | Lippert |
| 9,950,137 B2 | 4/2018 | Lippert |
| 10,252,024 B2 | 4/2019 | Northrop |
| 10,363,389 B2 | 7/2019 | Lippert et al. |
| 10,639,456 B2 | 5/2020 | Peralta |
| 2001/0009980 A1 | 7/2001 | Richardson et al. |
| 2002/0013540 A1 | 1/2002 | Jacobsen et al. |
| 2002/0019599 A1 | 2/2002 | Rooney |
| 2002/0049392 A1 | 4/2002 | DeMello |
| 2002/0062524 A1 | 5/2002 | Vogland et al. |
| 2002/0078808 A1 | 6/2002 | Jacobsen et al. |
| 2002/0082524 A1 | 6/2002 | Anderson |
| 2003/0009208 A1 | 1/2003 | Snyder et al. |
| 2003/0023190 A1 | 1/2003 | Cox |
| 2003/0069522 A1 | 4/2003 | Jacobsen |
| 2003/0093059 A1 | 5/2003 | Griffin et al. |
| 2003/0125641 A1 | 7/2003 | Jafari et al. |
| 2004/0039371 A1 | 2/2004 | Tockman et al. |
| 2004/0054349 A1 | 3/2004 | Brightbili |
| 2004/0087933 A1 | 5/2004 | Lee |
| 2004/0093060 A1 | 5/2004 | Seguin et al. |
| 2004/0102719 A1 | 5/2004 | Keith et al. |
| 2004/0111044 A1 | 6/2004 | Davis et al. |
| 2004/0122340 A1 | 6/2004 | Vrba et al. |
| 2004/0167440 A1 | 8/2004 | Sharrow et al. |
| 2004/0181174 A2 | 9/2004 | Davis |
| 2004/0186485 A1 | 9/2004 | Kear |
| 2004/0193140 A1 | 9/2004 | Griffin |
| 2004/0225292 A1 | 11/2004 | Sasso et al. |
| 2004/0254450 A1 | 12/2004 | Griffin et al. |
| 2005/0054953 A1 | 3/2005 | Ryan |
| 2005/0124976 A1 | 6/2005 | Devens, Jr. et al. |
| 2005/0216049 A1 | 9/2005 | Jones et al. |
| 2005/0274384 A1 | 12/2005 | Tran et al. |
| 2006/0041186 A1 | 2/2006 | Vancaillie |
| 2006/0074442 A1 | 4/2006 | Noriega |
| 2006/0089618 A1 | 4/2006 | McFerran |
| 2006/0112802 A1 | 6/2006 | Fujinami |
| 2006/0121218 A1 | 6/2006 | Obara et al. |
| 2006/0189896 A1 | 8/2006 | Davis et al. |
| 2006/0241519 A1 | 10/2006 | Hojeibane et al. |
| 2006/0247661 A1 | 11/2006 | Richards et al. |
| 2006/0262474 A1 | 11/2006 | Chen et al. |
| 2007/0010786 A1 | 1/2007 | Casey et al. |
| 2007/0100285 A1 | 5/2007 | Griffin |
| 2007/0112331 A1 | 5/2007 | Weber et al. |
| 2007/0135763 A1 | 6/2007 | Musbach |
| 2007/0142893 A1 | 6/2007 | Buiser et al. |
| 2007/0167876 A1 | 7/2007 | Euteneuer et al. |
| 2007/0185415 A1 | 8/2007 | Ressemann et al. |
| 2007/0221230 A1 | 9/2007 | Thompson |
| 2007/0233039 A1 | 10/2007 | Mitelberg |
| 2007/0250036 A1 | 10/2007 | Volk |
| 2007/0287955 A1 | 12/2007 | Layman et al. |
| 2008/0021347 A1 | 1/2008 | Jacobsen et al. |
| 2008/0021401 A1* | 1/2008 | Jacobsen ............... A61M 25/01 604/164.13 |
| 2008/0021404 A1 | 1/2008 | Jacobsen et al. |
| 2008/0064989 A1 | 3/2008 | Chen et al. |
| 2008/0077049 A1 | 3/2008 | Hirshman |
| 2008/0086854 A1 | 4/2008 | Boyd |
| 2008/0097246 A1 | 4/2008 | Stafford |
| 2008/0097247 A1 | 4/2008 | Eskuri |
| 2008/0097248 A1 | 4/2008 | Munoz |
| 2008/0119869 A1 | 5/2008 | Teague et al. |
| 2008/0122226 A1 | 5/2008 | Madison |
| 2008/0125674 A1 | 5/2008 | Bilecen et al. |
| 2008/0147170 A1 | 6/2008 | Vrba |
| 2008/0188298 A1 | 8/2008 | Seelig et al. |
| 2008/0188928 A1 | 8/2008 | Salahieh |
| 2008/0200839 A1 | 8/2008 | Bunch et al. |
| 2008/0262474 A1 | 10/2008 | Northrop |
| 2008/0269641 A1 | 10/2008 | O'Shaughnessy et al. |
| 2008/0319525 A1 | 12/2008 | Tieu |
| 2009/0036832 A1 | 2/2009 | Skujins et al. |
| 2009/0036833 A1 | 2/2009 | Parins |
| 2009/0043283 A1 | 2/2009 | Turnlund et al. |
| 2009/0043372 A1 | 2/2009 | Northrop et al. |
| 2009/0118675 A1 | 5/2009 | Czyscon et al. |
| 2009/0177119 A1 | 7/2009 | Heidner |
| 2009/0177185 A1 | 7/2009 | Northrop |
| 2009/0254000 A1 | 10/2009 | Layman et al. |
| 2009/0292225 A1 | 11/2009 | Chen et al. |
| 2009/0318892 A1 | 12/2009 | Aboytes et al. |
| 2010/0063479 A1 | 3/2010 | Merddan |
| 2010/0114017 A1 | 5/2010 | Lenker et al. |
| 2010/0114302 A1 | 5/2010 | Tzafriri et al. |
| 2010/0139465 A1 | 6/2010 | Christian et al. |
| 2010/0228150 A1 | 9/2010 | Zimmerman |
| 2010/0256527 A1 | 10/2010 | Lippert et al. |
| 2010/0256528 A1* | 10/2010 | Lippert ............... A61B 18/1492 600/585 |
| 2010/0256601 A1 | 10/2010 | Lippert et al. |
| 2010/0256602 A1 | 10/2010 | Lippert et al. |
| 2010/0256603 A1 | 10/2010 | Lippert |
| 2010/0256604 A1 | 10/2010 | Lippert |
| 2010/0256605 A1 | 10/2010 | Lippert et al. |
| 2010/0256606 A1 | 10/2010 | Lippert et al. |
| 2010/0318066 A1 | 12/2010 | Miyata et al. |
| 2011/0011226 A1 | 1/2011 | Tsurusawa |
| 2011/0022003 A1 | 1/2011 | Tekulve |
| 2011/0160680 A1 | 6/2011 | Cage et al. |
| 2011/0251519 A1 | 10/2011 | Romoscanu |
| 2012/0065623 A1 | 3/2012 | Nelson, III |
| 2012/0158034 A1 | 6/2012 | Wilson |
| 2012/0209073 A1 | 8/2012 | McWeeney et al. |

(56) References Cited

U.S. PATENT DOCUMENTS

| | | |
|---|---|---|
| 2012/0239074 A1 | 9/2012 | Aboytes et al. |
| 2012/0271397 A1 | 10/2012 | Muzslay et al. |
| 2013/0018359 A1 | 1/2013 | Coyle |
| 2013/0096553 A1 | 4/2013 | Hill et al. |
| 2013/0110000 A1 | 5/2013 | Tully |
| 2013/0226033 A1 | 8/2013 | Eskuri |
| 2013/0255456 A1 | 10/2013 | Christian |
| 2014/0094787 A1 | 4/2014 | Reynolds |
| 2014/0187983 A1 | 7/2014 | Anderson |
| 2014/0257363 A1 | 9/2014 | Lippert |
| 2014/0276109 A1 | 9/2014 | Gregorich |
| 2014/0276787 A1 | 9/2014 | Wang et al. |
| 2014/0309657 A1 | 10/2014 | Ben-Ami |
| 2014/0336620 A1 | 11/2014 | Layman et al. |
| 2015/0011834 A1 | 1/2015 | Ayala et al. |
| 2015/0011964 A1 | 1/2015 | Abner |
| 2015/0190614 A1 | 7/2015 | Uihlein |
| 2015/0216533 A1 | 8/2015 | Gray et al. |
| 2015/0238734 A1 | 8/2015 | Kanazawa |
| 2015/0290432 A1 | 10/2015 | Matthews |
| 2015/0297863 A1 | 10/2015 | Hannon et al. |
| 2015/0305710 A1 | 10/2015 | Koninklijke |
| 2015/0306355 A1 | 10/2015 | Idstrom |
| 2016/0008585 A1 | 1/2016 | Tano |
| 2016/0045101 A1* | 2/2016 | Nakatate ........ A61B 5/6851 600/478 |
| 2016/0089128 A1 | 3/2016 | Weber et al. |
| 2016/0113793 A1 | 4/2016 | Nishigishi |
| 2016/0135827 A1 | 5/2016 | Elsesser |
| 2016/0199620 A1 | 7/2016 | Pokorney |
| 2016/0235337 A1 | 8/2016 | Govari |
| 2016/0361520 A1 | 12/2016 | Braun |
| 2016/0367788 A1 | 12/2016 | Jimenez et al. |
| 2016/0375226 A1 | 12/2016 | Nabeshima |
| 2017/0189643 A1 | 7/2017 | Christian |
| 2017/0281909 A1 | 10/2017 | Northrop et al. |
| 2018/0015261 A1 | 1/2018 | Lippert |
| 2018/0015262 A1 | 1/2018 | Lippert |
| 2018/0015263 A1 | 1/2018 | Lippert |
| 2018/0028177 A1* | 2/2018 | van Oepen ....... A61M 25/0136 |
| 2018/0071496 A1 | 3/2018 | Snyder |
| 2018/0177517 A1 | 6/2018 | Lippert |
| 2018/0185619 A1 | 7/2018 | Batman et al. |
| 2018/0193607 A1 | 7/2018 | Lippert |
| 2019/0290883 A1 | 9/2019 | Lippert et al. |
| 2020/0094027 A1 | 3/2020 | Davis |
| 2020/0121308 A1 | 4/2020 | Davis et al. |
| 2020/0222672 A1 | 7/2020 | Davis et al. |
| 2020/0345975 A1 | 11/2020 | Snyder |
| 2021/0162184 A1 | 6/2021 | Lippert et al. |
| 2021/0178128 A1 | 6/2021 | Lippert et al. |
| 2021/0213241 A1 | 7/2021 | Christian et al. |
| 2021/0228845 A1 | 7/2021 | Lippert et al. |
| 2021/0283380 A1 | 9/2021 | Lippert et al. |
| 2021/0346656 A1 | 11/2021 | Lippert et al. |

FOREIGN PATENT DOCUMENTS

| | | |
|---|---|---|
| AU | 774559 | 7/2004 |
| AU | 2008229892 | 10/2008 |
| BR | 9709363 | 1/2000 |
| BR | 9712829 | 1/2000 |
| CA | 2266685 | 5/2006 |
| CA | 2255781 | 3/2007 |
| CA | 2395149 | 12/2008 |
| CN | 1230914 | 10/1999 |
| CN | 1324285 | 11/2001 |
| CN | 1422673 | 6/2003 |
| CN | 1518428 | 8/2004 |
| CN | 1781684 | 6/2006 |
| CN | 1897892 A | 1/2007 |
| CN | 101001660 | 7/2007 |
| CN | 101209365 A | 7/2008 |
| CN | 101304778 | 11/2008 |
| CN | 201239164 Y | 5/2009 |
| CN | 101815553 A | 8/2010 |
| CN | 102049085 A | 5/2011 |
| CN | 102107041 A | 6/2011 |
| CN | 102824681 A | 12/2012 |
| CN | 102847225 A | 1/2013 |
| CN | 103764012 A | 4/2014 |
| CN | 103860265 A | 6/2014 |
| CN | 104271035 A | 1/2015 |
| CN | 104602616 A | 5/2015 |
| CN | 105209102 A | 12/2015 |
| CN | 105545375 A | 5/2016 |
| CN | 105682729 A | 6/2016 |
| CN | 105828690 A | 8/2016 |
| CN | 105979880 A | 9/2016 |
| DE | 60036882 | 7/2008 |
| DE | 69738235 | 7/2008 |
| EP | 0521595 A2 | 1/1993 |
| EP | 0998323 A1 | 5/2000 |
| EP | 934141 | 11/2005 |
| EP | 921754 | 10/2007 |
| EP | 1239901 | 10/2007 |
| EP | 1940498 | 7/2008 |
| EP | 2964305 | 1/2016 |
| ES | 2293660 | 3/2008 |
| JP | 59102509 | 6/1984 |
| JP | 06-154335 A | 6/1994 |
| JP | 07-008560 | 1/1995 |
| JP | 08-308934 | 11/1996 |
| JP | 11294497 | 10/1999 |
| JP | 2000116787 | 4/2000 |
| JP | 2000511094 | 8/2000 |
| JP | 2000343313 | 12/2000 |
| JP | 2001500808 | 1/2001 |
| JP | 2002543896 | 12/2002 |
| JP | 2003011117 | 1/2003 |
| JP | 2004-025340 A | 1/2004 |
| JP | 2004136121 | 5/2004 |
| JP | 2004329552 | 11/2004 |
| JP | 2004535233 | 11/2004 |
| JP | 2005-514115 A | 5/2005 |
| JP | 2005533594 | 11/2005 |
| JP | 2007313638 | 12/2007 |
| JP | 2008536639 | 9/2008 |
| JP | 2010-029736 A | 2/2010 |
| JP | 2010-503484 A | 2/2010 |
| JP | 2010-535583 A | 11/2010 |
| JP | 2010535588 | 11/2010 |
| JP | 2011-206175 A | 10/2011 |
| JP | 4805208 | 11/2011 |
| JP | 4845313 | 12/2011 |
| JP | 2013-523282 A | 6/2013 |
| JP | 2015-181723 A | 10/2015 |
| KR | 20000015896 | 3/2000 |
| KR | 20000036139 | 6/2000 |
| TW | 412468 | 11/2000 |
| WO | 9419039 | 1/1994 |
| WO | 1994006503 | 3/1994 |
| WO | 97/43949 A1 | 11/1997 |
| WO | 98/58697 A1 | 12/1998 |
| WO | 99/04847 A1 | 2/1999 |
| WO | 9953824 | 10/1999 |
| WO | 2004011076 | 2/2004 |
| WO | 2006/025931 A1 | 3/2006 |
| WO | 2006113863 | 10/2006 |
| WO | 2007050718 | 5/2007 |
| WO | 2008/034010 A2 | 3/2008 |
| WO | 2009/020691 A2 | 2/2009 |
| WO | 2009/020836 A1 | 2/2009 |
| WO | 2009020961 | 2/2009 |
| WO | 2009020962 | 2/2009 |
| WO | 2010077692 | 7/2010 |
| WO | 2010115163 | 10/2010 |
| WO | 2011/123689 A1 | 10/2011 |
| WO | 2014/005095 A1 | 1/2014 |
| WO | 2014066104 | 5/2014 |
| WO | 2014138580 | 9/2014 |
| WO | 2016047499 | 3/2016 |
| WO | 2016117238 | 7/2016 |

(56) References Cited

FOREIGN PATENT DOCUMENTS

| WO | 2016136609 | 9/2016 |
| WO | 2016152194 | 9/2016 |
| WO | 2016158671 | 10/2016 |
| WO | 2018/017349 A1 | 1/2018 |
| WO | 2018218216 | 11/2018 |
| WO | 2020/217171 A1 | 10/2020 |

OTHER PUBLICATIONS

International Search Report and Written Opinion for PCT/US2019/021031 dated Jun. 18, 2019.
U.S. Appl. No. 15/848,878, Oct. 29, 2019, Office Action.
U.S. Appl. No. 15/611,344, Nov. 12, 2019, Final Office Action.
U.S. Appl. No. 15/698,553, May 15, 2020, Notice of Allowance.
U.S. Appl. No. 15/611,344, May 21, 2020, Office Action.
U.S. Appl. No. 15/698,553, Nov. 27, 2019, Office Action.
U.S. Appl. No. 15/848,878, Feb. 5, 2020, Office Action.
U.S. Appl. No. 16/212,425, Mar. 16, 2020, Office Action.
U.S. Appl. No. 16/212,425, filed Dec. 6, 2018, Christian.
Canadian Office Action for CA2757655 dated Jan. 2, 2018.
EP10759515.9 Supplementary European Search Report dated Sep. 25, 2012.
European Search Report for EP09836735 dated Nov. 7, 2012.
Supplementary Partial European Search Report for EP14760849 dated Oct. 11, 2016.
European Search Report for EP15197042.3 dated Apr. 11, 2016.
European Search Report for application No. 17184064.8 dated Jan. 5, 2018.
International Search Report and Written Opinion for PCT/US2009/067217 dated Dec. 16, 2010.
International Search Report and Written Opinion for PCT/US2010/029867 dated Jun. 1, 2010.
International Search Report and Written Opinion for PCT/US2014/021742 dated Aug. 27, 2014.
International Search Report and Written Opinion for PCT/US2017/041299 dated Oct. 2, 2017.
International Search Report and Written Opinion for PCT/US2017/041301 dated Oct. 2, 2017.
International Search Report and Written Opinion for PCT/US2017/041305 dated Oct. 2, 2017.
International Search Report and Written Opinion for application PCT/US2017/050802 dated Nov. 7, 2017.
International Search Report and Written Opinion for PCT/US2017/068056 dated Feb. 26, 2018.
International Search Report and Written Opinion for PCT/US2018/034723 dated Sep. 5, 2018.
International Search Report and Written Opinion for PCT/US2018/034756 dated Aug. 14, 2018.
U.S. Appl. No. 12/633,727, Oct. 16, 2012, Office Action.
U.S. Appl. No. 12/633,727, Feb. 28, 2013, Notice of Allowance.
U.S. Appl. No. 12/753,831, Feb. 1, 2012, Office Action.
U.S. Appl. No. 12/753,831, May 31, 2012, Final Office Action.
U.S. Appl. No. 12/753,831, Mar. 21, 2014, Office Action.
U.S. Appl. No. 12/753,831, Aug. 29, 2014, Final Office Action.
U.S. Appl. No. 12/753,831, Apr. 14, 2015, Notice of Allowance.
U.S. Appl. No. 12/753,836, Dec. 9, 2011, Office Action.
U.S. Appl. No. 12/753,836, May 1, 2012, Final Office Action.
U.S. Appl. No. 12/753,836, Jul. 31, 2014, Office Action.
U.S. Appl. No. 12/753,836, Jan. 9, 2015, Final Office Action.
U.S. Appl. No. 12/753,836, Jun. 26, 2015, Office Action.
U.S. Appl. No. 12/753,836, Feb. 17, 2016, Final Office Action.
U.S. Appl. No. 12/753,836, Dec. 23, 2016, Office Action.
U.S. Appl. No. 12/753,836, Jul. 14, 2017, Final Office Action.
U.S. Appl. No. 12/753,836, Nov. 24, 2017, Notice of Allowance.
U.S. Appl. No. 12/753,839, Feb. 7, 2012, Office Action.
U.S. Appl. No. 12/753,839, May 31, 2012, Final Office Action.
U.S. Appl. No. 12/753,839, May 5, 2014, Office Action.
U.S. Appl. No. 12/753,842, Aug. 1, 2012, Office Action.
U.S. Appl. No. 12/753,842, Jan. 9, 2013, Final Office Action.
U.S. Appl. No. 12/753,842, Jan. 29, 2014, Office Action.
U.S. Appl. No. 12/753,842, Sep. 4, 2014, Final Office Action.
U.S. Appl. No. 12/753,842, Dec. 29, 2014, Notice of Allowance.
U.S. Appl. No. 12/753,842, Mar. 5, 2015, Notice of Allowance.
U.S. Appl. No. 12/753,849, May 10, 2011, Office Action.
U.S. Appl. No. 12/753,849, Oct. 18, 2011, Office Action.
U.S. Appl. No. 12/753,849, Jun. 6, 2012, Final Office Action.
U.S. Appl. No. 12/753,849, Jan. 3, 2013, Office Action.
U.S. Appl. No. 12/753,849, Oct. 9, 2013, Final Office Action.
U.S. Appl. No. 12/753,849, May 27, 2014, Office Action.
U.S. Appl. No. 12/753,849, Nov. 5, 2014, Interview Summary.
U.S. Appl. No. 12/753,849, Feb. 2, 2015, Notice of Allowance.
U.S. Appl. No. 12/753,849, Apr. 30, 2015, Notice of Allowance.
U.S. Appl. No. 12/753,855, Sep. 15, 2011, Office Action.
U.S. Appl. No. 12/753,855, Apr. 18, 2012, Final Office Action.
U.S. Appl. No. 12/753,855, Feb. 28, 2014, Office Action.
U.S. Appl. No. 12/753,855, Jan. 13, 2015, Final Office Action.
U.S. Appl. No. 12/753,855, May 21, 2015, Office Action.
U.S. Appl. No. 12/753,855, May 5, 2016, Office Action.
U.S. Appl. No. 12/753,855, Nov. 30, 2016, Notice of Allowance.
U.S. Appl. No. 12/753,858, May 10, 2011, Office Action.
U.S. Appl. No. 12/753,858, Oct. 19, 2011, Final Office Action.
U.S. Appl. No. 12/753,858, Feb. 3, 2012, Office Action.
U.S. Appl. No. 12/753,858, Jul. 18, 2012, Final Office Action.
U.S. Appl. No. 12/753,858, Mar. 29, 2013, Office Action.
U.S. Appl. No. 12/753,858, Jan. 17, 2014, Final Office Action.
U.S. Appl. No. 12/753,858, Sep. 4, 2014, Office Action.
U.S. Appl. No. 12/753,858, Nov. 4, 2014, Interview Summary.
U.S. Appl. No. 12/753,858, May 28, 2015, Final Office Action.
U.S. Appl. No. 12/753,858, Dec. 30, 2015, Office Action.
U.S. Appl. No. 12/753,858, Oct. 24, 2016, Office Action.
U.S. Appl. No. 12/753,858, Mar. 27, 2017, Office Action.
U.S. Appl. No. 12/753,858, Oct. 20, 2017, Final Office Action.
U.S. Appl. No. 12/753,858, Mar. 13, 2018, Office Action.
U.S. Appl. No. 12/753,858, Nov. 14, 2018, Final Office Action.
U.S. Appl. No. 12/753,858, Mar. 14, 2019, Notice of Allowance.
U.S. Appl. No. 13/901,375, Dec. 10, 2015, Office Action.
U.S. Appl. No. 13/901,375, Aug. 1, 2016, Office Action.
U.S. Appl. No. 13/901,375, Dec. 27, 2016, Notice of Allowance.
U.S. Appl. No. 14/199,675, Nov. 3, 2016, Office Action.
U.S. Appl. No. 14/199,675, May 18, 2017, Final Office Action.
U.S. Appl. No. 14/199,675, Sep. 6, 2017, Notice of Allowance.
U.S. Appl. No. 15/465,399, Apr. 23, 2018, Office Action.
U.S. Appl. No. 15/465,399, Sep. 10, 2018, Notice of Allowance.
U.S. Appl. No. 15/611,328, Mar. 27, 2019, Office Action.
U.S. Appl. No. 15/611,328, Sep. 24, 2019, Final Office Action.
U.S. Appl. No. 15/611,344, Mar. 26, 2019, Office Action.
U.S. Appl. No. 16/281,046, filed Feb. 20, 2019, Snyder.
U.S. Appl. No. 16/439,894, filed Jun. 13, 2019, Lippert.
International Search Report and Written Opinion for PCT/US2019/019046 dated May 17, 2019.
U.S. Appl. No. 15/606,607, May 14, 2019, Office Action.
International Search Report and Written Opinion for Application PCT/US2017/050602 dated Nov. 7, 2017.
International Search Report and Written Opinion received for PCT Patent Application No. PCT/US2020/030589, dated Jul. 17, 2020, 7 pages.
International Search Report and Written Opinion, PCT App. No. PCT/US2020/013754, dated Jun. 9, 2020, 11 pages.
Non-Final Office Action received for U.S. Appl. No. 15/606,607, dated Jun. 10, 2020, 26 pages.
Office Action received for U.S. Appl. No. 12/753,858, dated Mar. 13, 2018.
Final Office Action received for U.S. Appl. No. 16/212,425, dated Aug. 3, 2020, 14 pages.
Final Office Action received for U.S. Appl. No. 15/848,878, dated Aug. 27, 2020, 13 pages.
Non-Final Office Action received for U.S. Appl. No. 15/611,328, dated Jun. 29, 2020, 13 pages.
Non-Final Office Action received for U.S. Appl. No. 15/917,255, dated Aug. 17, 2020, 12 pages.
Final Rejection received for U.S. Appl. No. 15/606,607, dated Dec. 15, 2020, 24 pages.

(56) References Cited

OTHER PUBLICATIONS

Non-Final Office Action received for U.S. Appl. No. 15/848,878, dated Jun. 3, 2021, 13 pages.
International Search Report and Written Opinion received for PCT Patent Application No. PCT/US21/14656, dated Apr. 28, 2021, 8 pages.
Non-Final Office Action received for U.S. Appl. No. 16/855,366, dated Jun. 23, 2021, 15 pages.
Non-Final Office Action received for U.S. Appl. No. 16/616,139, dated Oct. 26, 2021, 11 pages.
Final Office Action received for U.S. Appl. No. 15/848,878, dated Sep. 22, 2021, 12 pages.
International Search Report and Written Opinion received for PCT Patent Application No. PCT/US21/042753, dated Nov. 5, 2021, 14 pages.

* cited by examiner

MICROFABRICATED CATHETER HAVING AN INTERMEDIATE PREFERRED BENDING SECTION

CROSS-REFERENCE TO RELATED APPLICATIONS

This application claims priority to and the benefit of U.S. Provisional Patent Application No. 62/633,939, filed Feb. 22, 2018 and titled "Microfabricated Catheter having an Intermediate Preferred Bending Section," the entirety of which is incorporated herein by this reference.

BACKGROUND

Interventional devices such as guidewires and catheters are frequently utilized in the medical field to perform delicate procedures deep within the human body. Typically, a catheter is inserted into a patient's femoral, radial, carotid, or jugular vessel and navigated through the patient's vasculature to the heart, brain, or other targeted anatomy as required. Often, a guidewire is first routed to the targeted anatomy, and one or more catheters are subsequently passed over the guidewire and routed to the targeted anatomy. Once in place, the catheter can be used to deliver drugs, stents, embolic devices, radiopaque dyes, or other devices or substances for treating the patient in a desired manner.

In many applications, such an interventional device must be angled through the tortuous bends and curves of a vasculature passageway to arrive at the targeted anatomy. Such an interventional device requires sufficient flexibility, particularly closer to its distal end, to navigate such tortuous pathways. However, other design aspects must also be considered. For example, the interventional device must also be able to provide sufficient torquability (i.e., the ability to transmit torque applied at the proximal end all the way to the distal end), pushability (i.e., the ability to transmit axial push to the distal end rather than bending and binding intermediate portions), and structural integrity for performing intended medical functions.

Several important medical procedures require delivery of a microcatheter to a coronary artery. For example, percutaneous coronary intervention (PCI) typically involves coronary catheterization to introduce a radiocontrast agent to the coronary arteries followed by coronary angioplasty. During coronary catheterization, a physician inserts a microcatheter into a patient's arterial vasculature using a transradial or transfemoral approach and guides the catheter into the aorta until the distal tip is just within the opening of one of the targeted coronary arteries. The radiocontrast agent is then delivered through the catheter and into the targeted coronary artery to enable medical personnel to visualize the associated cardiac vasculature (e.g., to visualize atheroma, calcification, and stenotic areas). During coronary angioplasty, the delivery catheter must likewise be routed into the aorta and further through the targeted coronary artery to the treatment site. Once at the treatment site, a balloon is inflated to reduce stenosis, and a stent may also be placed.

Such delicate procedures require precise control of the delivery catheter. However, due to the inherent tortuosity of the cardiac vascular anatomy involved, it can be difficult to get the catheter properly positioned at the targeted treatment site. In particular, once the distal tip of the catheter has reached a position near the aortic root, the catheter must sharply curve to align with and enter either coronary artery. To address this challenge, conventional guide catheters include a pre-curved terminal portion having a single or compound curve. Differences in clinical procedure, patient anatomy, and approach (radial vs. femoral) have led to a vast array of different PCI guide catheters. Each particular design, however, may lack operational versatility and thus only properly function in a narrow set of circumstances. Difficulties thus exist in stabilizing the guide catheter and aligning its distal tip with the targeted coronary ostium. Accordingly, there has been a long felt and ongoing need for a microcatheter device having improved guidance and positioning capabilities with a versatile design enabling effective use in a variety of circumstances.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

I. Introduction

The present disclosure relates to interventional catheter devices having features that provide for effective positioning at the aortic root and effective access to a targeted coronary artery. Although many of the embodiments are described in the specific context of being positioned near the aortic root, it will be understood that the described devices are not limited solely to such applications. The catheter devices described herein may therefore be utilized in other applications where the positioning benefits of the device may be advantageous.

Embodiments described herein include different catheter sections of varied construction that are arranged to provide functional positioning benefits. The following description refers to a proximal section, an intermediate section, and a distal section. The intermediate section includes two subsections which collectively form the intermediate section. As used herein, the proximal-intermediate section is the more proximal part of the intermediate section which couples to the proximal section of the catheter and extends distally therefrom. The distal-intermediate section is the more distal part of the intermediate section which couples to the distal section of the catheter and extends proximally therefrom.

As described in more detail below, the intermediate section includes features which enable effective positioning and stabilization of the catheter at a position in the aorta near the aortic root. In particular, the proximal-intermediate section includes a preferred bending axis allowing it to flex in one plane at the base of the aortic root, and the distal-intermediate section includes a relatively rigid construction to provide support across the base of the aortic root.

As used herein, references to components or features which are configured to get progressively wider, narrower, shallower, deeper, more or less flexible, etc., are intended to disclose components or features which, on average, progress in the manner described. Accordingly, embodiments that include one or more areas that depart from the overall average progression are still within the scope of the description. For example, references to a component or feature that progressively changes in some manner as it gets closer to one end of the device may be considered to progressively change, on average, if the change is apparent over at least about 0.5, 1, 3, or 5 cm of axial length of the device, or over an axial length within a range defined by any two of the foregoing values.

II. Catheter Positioning at the Aortic Root

Figure 1A:
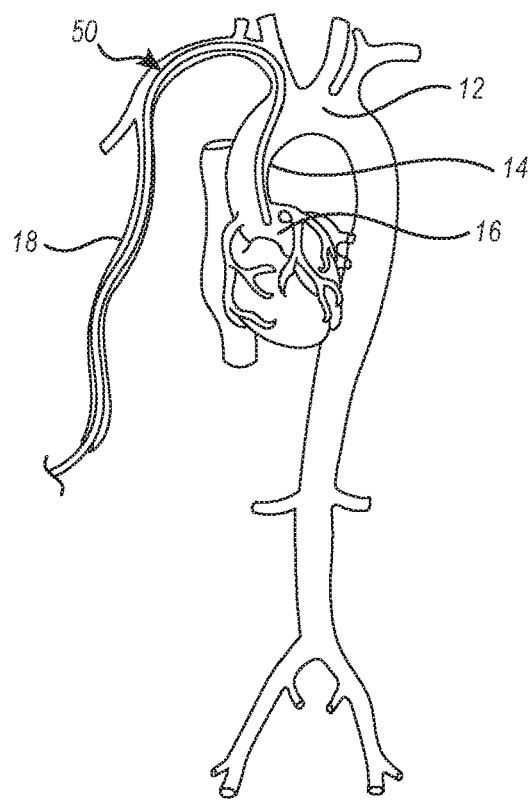
FIG. 1A schematically illustrates human arterial vasculature showing a transradial approach of a catheter to a position near the aortic root.
Figure 1B:
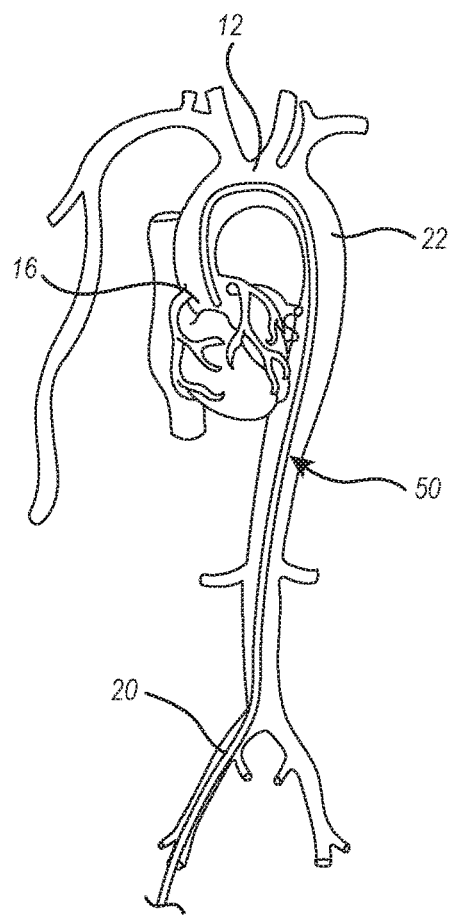
FIG. 1B schematically illustrates human arterial vasculature showing a transfemoral approach of a catheter to a position near the aortic root.

FIGS. 1A and 1B illustrate possible transvascular approaches for reaching the aortic root. FIG. 1A shows a transradial approach, where the catheter 50 is inserted into the radial artery 18 (typically the right radial artery) and passed into the corresponding subclavian artery and then into the aortic arch 12. From the aortic arch 12, the distal tip of the catheter 50 is further directed into the ascending aorta 14 and to the aortic root 16. FIG. 1B illustrates a transfemoral approach, where the catheter 50 is inserted into the femoral artery 20, then passed retrograde into the descending aorta 22, and further directed around the aortic arch 12 and toward the aortic root 16. Though these are the most common approaches, other approaches may also be utilized (e.g., a transbrachial approach). The particular approach utilized may depend on physician preference, patient anatomy, procedural necessities, and the like. The catheter embodiments described herein may be utilized for any such approach to the aortic root 16.

Figure 2:
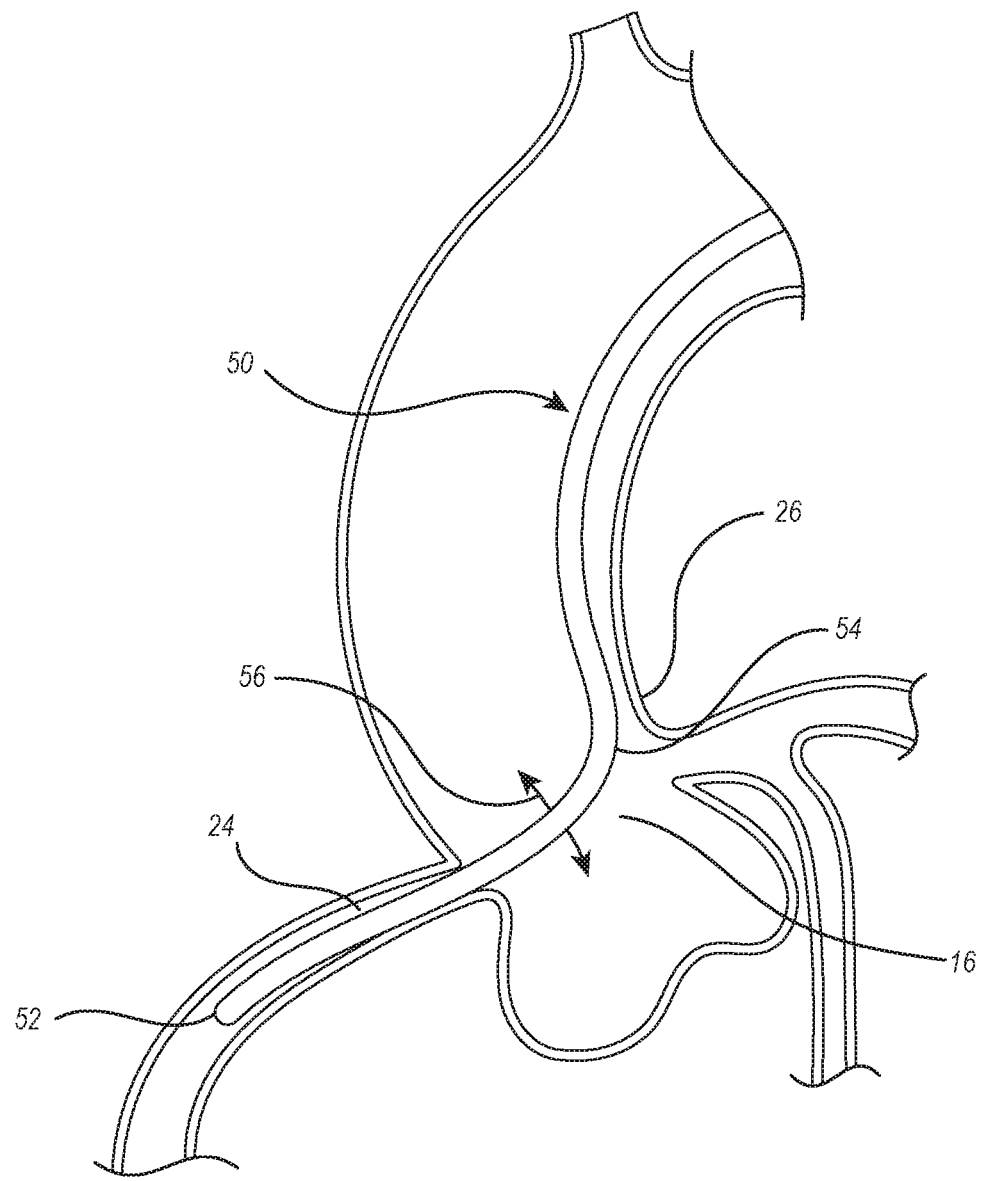
FIG. 2 illustrates an enlarged view of the aorta, showing a desired positioning of the catheter within the aorta for accessing a coronary artery.

FIG. 2 illustrates a preferred catheter position near the aortic root 16. Once the distal tip 52 of the catheter 50 has reached the aortic root 16, the procedure usually requires further passage into one of the coronary arteries. FIG. 2 illustrates entry into the right coronary artery 24; however, catheter embodiments described herein may also be utilized to access the left coronary artery in procedures where such access is desired. As shown, a portion of the catheter 50 preferably contacts the aortic wall at a point 26 opposite the targeted coronary artery (the right coronary artery 24 in this example).

This contact beneficially supports and stabilizes the catheter 50. However, achieving this position introduces its own challenges. From the point of contact 26 against the aortic wall opposite the targeted coronary artery 24, the catheter 50 must provide a relatively sharp bend 54 to extend across the aortic root 16 and reach the artery 24. The catheter 50 must be flexible enough to provide the illustrated bend 54. However, excessive flexibility in the portion of the catheter extending across the aortic root 16 may leave that portion subject to "sagging" or "bouncing" movements, as indicated by arrows 56. These undesirable movements can affect the position of the distal tip 52 further within the coronary artery 24, and may also cause the more proximal sections to move or bounce off of the stabilizing aortic wall at the point of contact 26. This can lead to more difficult device placement, procedural inaccuracies, and even trauma to the surrounding vasculature.

As described in further detail below, the catheter embodiments described herein include features which minimize or eliminate the foregoing limitations. The catheter device embodiments may be utilized to provide stable, effective catheter placement at the aortic root, which may allow more accurate and effective access to coronary arteries and better procedural outcomes.

III. Exemplary Catheter Device

Figure 3:
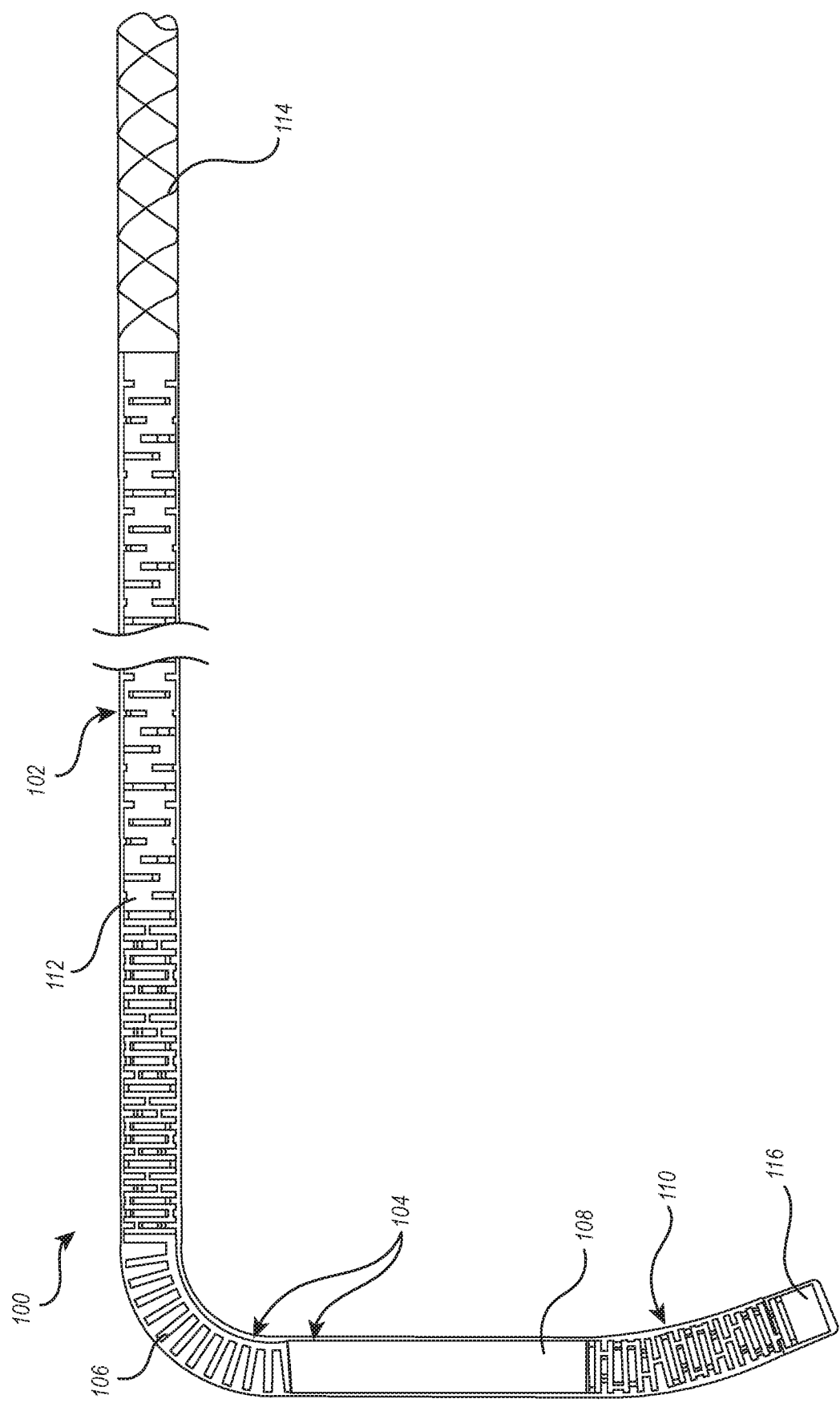
FIG. 3 illustrates an exemplary catheter device which may be utilized for accessing a coronary artery, the catheter device having a proximal section, a preferred bending intermediate section, a rigid intermediate section, and a flexible distal section.

FIG. 3 illustrates an exemplary embodiment of a catheter 100 capable of effective positioning at the aortic root. The illustrated catheter 100 includes a proximal section 102, an intermediate section 104, and a distal section 110. The proximal section 102 is further divided into a braided region 114 and a microfabricated region 112. The braided region 114 may be bonded to the microfabricated region 112 by including a machined-down step (not shown) in the catheter where the braid may be bonded to the catheter using epoxy or other suitable adhesive. As shown, the intermediate section is further divided into a proximal-intermediate section 106 and a distal-intermediate section 108. The microfabricated region 112 of the proximal section 102 includes features that provide flexibility while maintaining sufficient strength for effective torquability and pushability of the device.

Possible cut patterns of the microfabricated region 112 are described in greater detail below. In the illustrated embodiment, the microfabricated region 112 has a two-beam configuration with successive beam pairs arranged to form a helical pattern along the length of the microfabricated region 112. As shown, spacing between cut pairs grows progressively narrower as the microfabricated region 112 extends closer to the intermediate section 104. This provides the microfabricated region 112 with progressively higher flexibility in the distal direction. The flexibility differential beneficially balances catheter strength with flexibility. In more proximal regions of the device, good torquability is important, and closer to the distal end of the device, flexibility becomes increasingly important.

The proximal-intermediate section 106 extends distally from the proximal section 102. The proximal-intermediate section 106 is configured to provide the bend at the aortic wall to enable the more distal sections of the catheter to extend across the aortic root and into the targeted coronary artery (see FIG. 2). In this embodiment, the proximal-intermediate section 106 includes cuts aligned on the same side, leaving a resulting "spine" and allowing the section to preferentially flex in one plane at the base of the aortic root.

Substantially limiting the bending axis to a single plane allows for easier alignment of the distal tip of the catheter with the opening of the targeted coronary artery.

The distal-intermediate section 108 is more rigid than both the proximal-intermediate section 106 and the distal section 110. This beneficially provides support as the catheter extends from the aortic wall across the base of the aortic root toward the opening of the targeted coronary artery. The higher rigidity of the distal-intermediate section 108 functions to limit movement of the catheter in that region, which enables more effective positioning of the distal tip of the catheter. In the illustrated embodiment, the distal-intermediate section 108 omits microfabricated cuts. Alternative embodiments may include some microfabricated cutting to provide a desired level of flexibility. However, even in such embodiments, the distal-intermediate section 108 preferably still has greater rigidity than both the distal section 110 and the proximal-intermediate section 106.

The distal section 110 extends from the distal-intermediate section 108 to an atraumatic distal tip 116 of the device. As with the microfabricated region 112 of the proximal section 102, the distal section 110 may include a microfabricated cut pattern to provide greater flexibility. In some embodiments, the distal section 110 is configured to have greater flexibility than the microfabricated region 112 of the proximal section 102. For example, as compared to the cuts in the microfabricated region 112, the cuts of the distal section may be deeper and/or more narrowly spaced.

Much of the catheter 100 may beneficially be formed of a single integral piece of stock material, with the different sections being defined by different cut patterns (or lack thereof) rather than by separate pieces joined together at connecting joints. For example, at least the distal section, intermediate section, and microfabricated region of the proximal section may be formed from the same integral piece of stock material.

In presently preferred embodiments, the catheter 100 is formed from a metals and/or alloys (e.g., nickel titanium), though other suitable medical-grade materials may also be used, including other medical-grade polymers such as polyetheretherketone (PEEK). In some embodiments, the catheter 100 is formed from a single piece of material, although in alternative embodiments two or more separate pieces of material may be joined together to form the catheter 100.

The catheter 100 may also include an outer laminate made from a suitable medical-grade material. In some embodiments, a polymer laminate of variable durometer forms an outer coating of the catheter 100. For example, the laminate may have a higher durometer along the proximal section 102 and a lower durometer along the distal section 110. The laminate may have an intermediate durometer along the intermediate section 104. Alternatively, the laminate along the proximal-intermediate section 106 may have a relatively low durometer (e.g., similar to that at the distal section 110) while the laminate along the distal-intermediate section 108 may have a relatively high durometer (e.g., similar to that at the proximal section 102). Some embodiments may also use laminate with various gradations of durometer and/or progressively changing durometer values. For example, the laminate along one or more sections may have a progressively decreasing durometer in the distal direction.

The catheter 100 may also include a liner made from a suitable medical-grade material. In one embodiment, the liner is formed from polytetrafluoroethylene (PTFE), though alternative liner materials may also be utilized. In some embodiments, a portion of the laminate and/or liner extend distally beyond the microfabricated stock material of the distal section 110 to form an atraumatic distal tip 116.

Although dimensions may be varied according to particular application needs, a typical embodiment may have a total length of about 70 to 120 cm. The proximal section 102 may have a length of about 60 to 90 cm, with about 50 to 80 cm of that length making up the braided region 114 and about 5 to 40 cm of that length making up the microfabricated region 112. The intermediate section 104 may have a length of about 2 to 5 cm, with about 1 to 3 cm of that length making up the proximal-intermediate section 106 and about 2 to 4 of that length making up the distal-intermediate section 108. The distal section 110 may have a length of about 1 to 3 cm. Likewise, although catheter sizes may be varied according to particular application needs, a typical embodiment may have a size of about 4 to 9 F. Embodiments having dimensions within these ranges provide for effective catheter positioning at the aortic root.

IV. Exemplary Cut Patterns

A. Beam Configurations

The various patterns described below may be utilized in the different microfabricated sections of the catheter 100. For example, the distal section 110 and/or the microfabricated region 112 of the proximal section 102 preferably include one or more of the below described microfabricated features.

The various microfabricated features form fenestrations arranged to increase flexibility of the catheter device while maintaining good torquability. Cut patterns described herein may have different configurations defined by the number of resulting longitudinal beams resulting from each set of cuts at a given longitudinal position along the device. For example, in a "two-beam" configuration, each cut location along the length of the device includes a pair of opposed cuts resulting in a pair of opposed, axially extending beams. Typically, the two beams within the resulting beam pair are symmetrically spaced about the circumference of the catheter (i.e., spaced about 180 degrees apart), though in other embodiments they may be differentially circumferentially spaced. Likewise, the triad of beams in a three-beam configuration are typically symmetrically spaced about the circumference by about 120 degrees, the set of beams in a four-beam configuration are typically spaced about the circumference by about 90 degrees, etcetera, though other embodiments may include differential circumferential spacing.

other manufacturing parameters being equal (e.g., similar materials, cut depth, cut spacing, etc.), a configuration having a greater number of beams will be less flexible but have greater capacity for transmitting torque. Embodiments may include multiple sections each having a different beam configuration to provide different respective flexibility characteristics and a desired flexibility gradient across the length of the device. At the same time, a particular section having a particular beam configuration can include cuts arranged to provide a flexibility gradient within the particular section itself. For example, longitudinal spacing between cuts may be progressively less at areas closer to the distal end of the device. In this manner, a device may be configured to provide a desired flexibility profile across the length of the device by including both inter- and intra-sectional flexibility gradients.

Figure 4A:
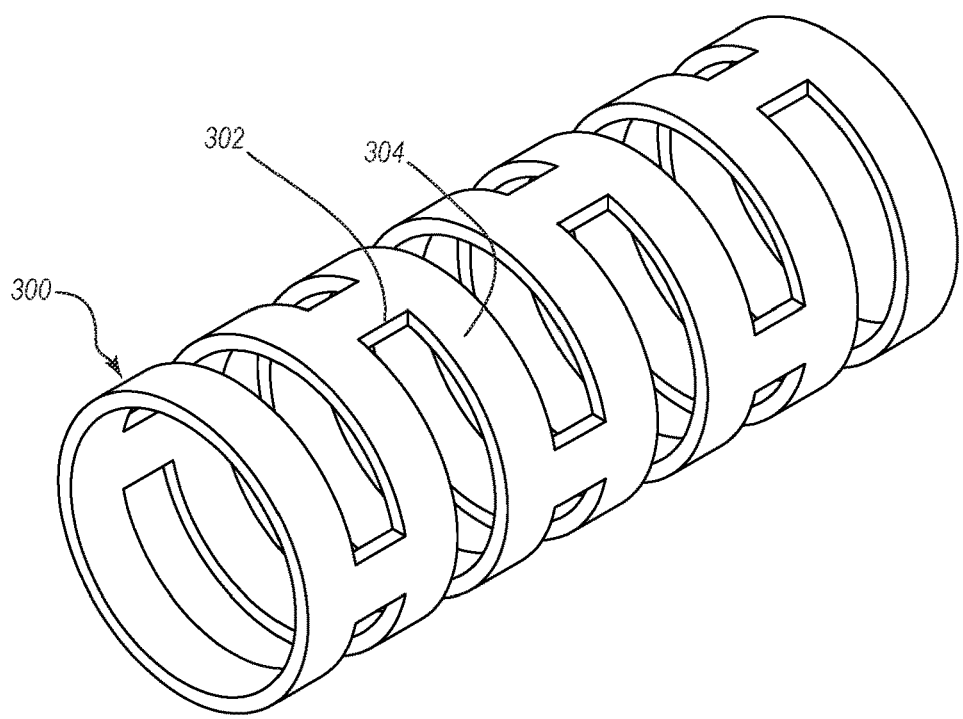
FIGS. 4A through 4D illustrate various beam configurations that may be utilized in various combinations to provide desired bending characteristics in the intravascular device.
Figure 4B:
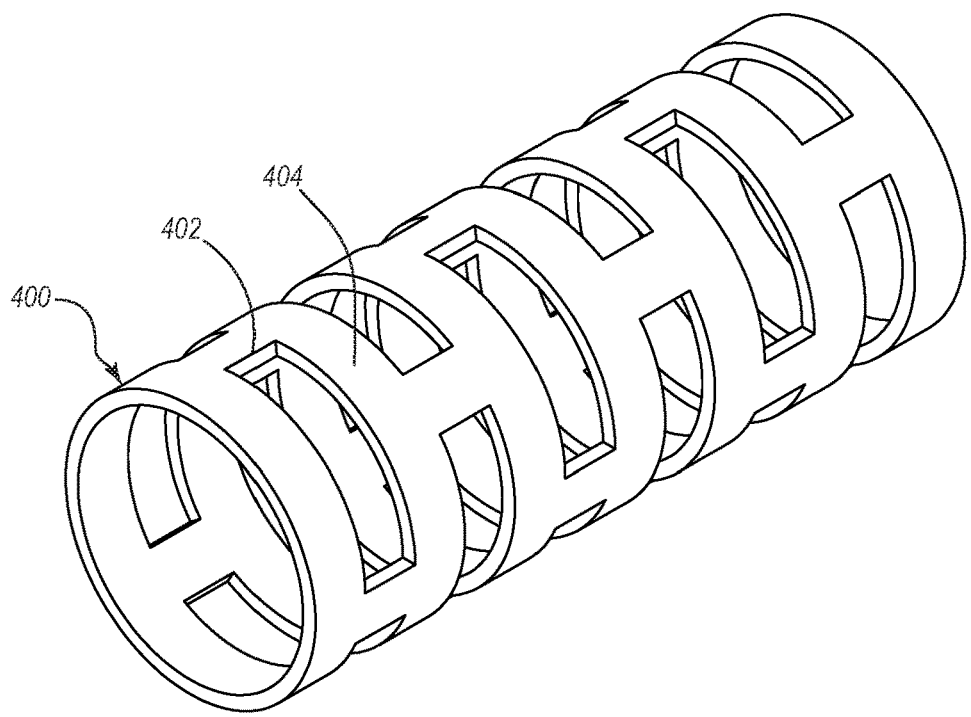
Figure 4C:
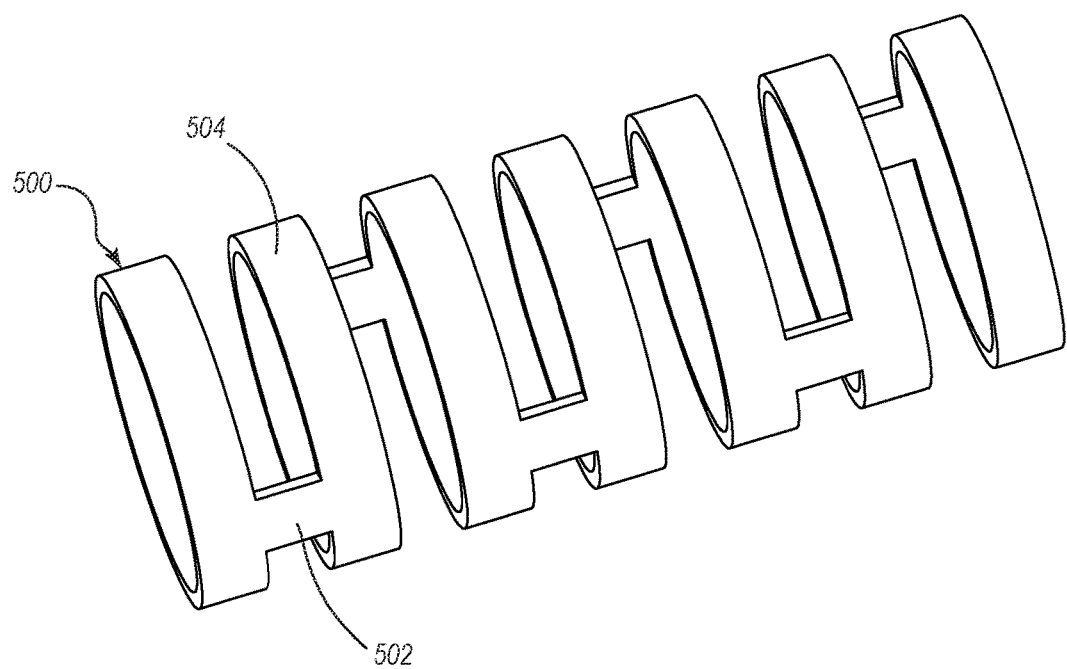
Figure 4D:
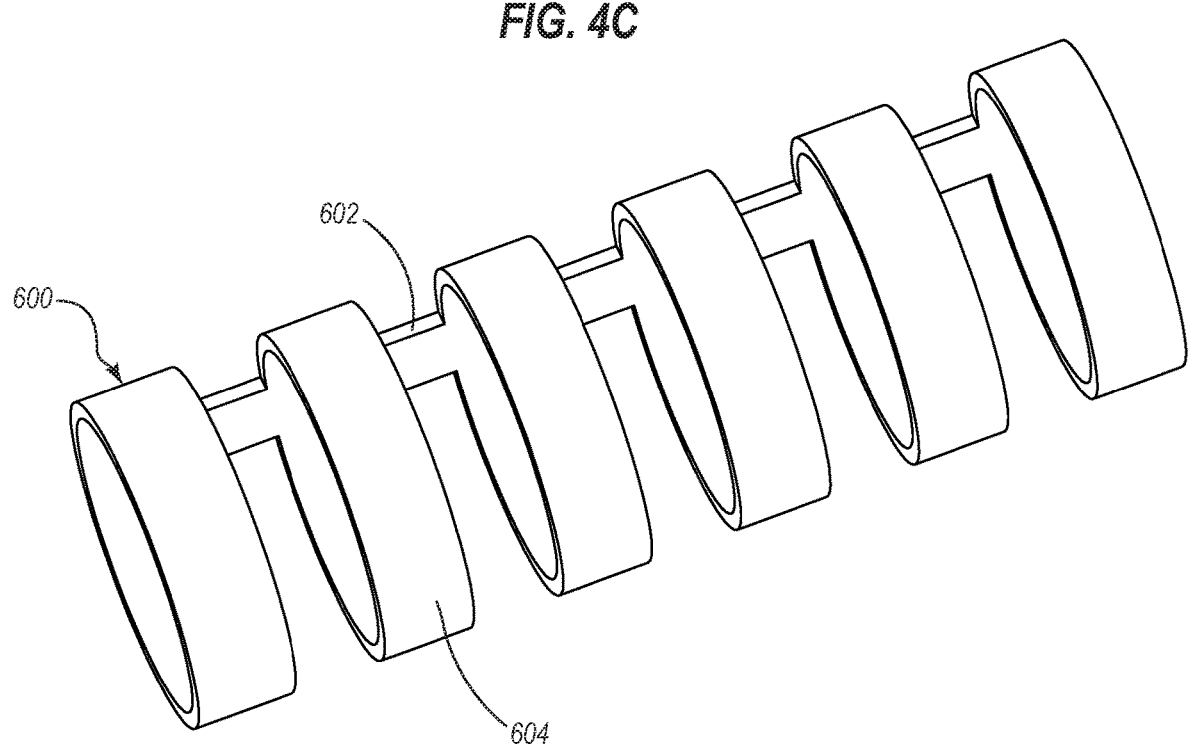

FIGS. 4A through 4D illustrate various embodiments of cut patterns which may be utilized in the devices described herein. FIG. 4A shows a "two-beam" configuration, FIG. 4B shows a "three-beam" configuration, and FIGS. 4C and 4D show different versions of a "one-beam" configuration.

Other embodiments may include configurations of more than three resulting beams per cut location (e.g., a "four-beam" cut pattern, "five-beam" cut pattern, etc.). All other manufacturing parameters being equal, the higher the number of resulting beams at each cut position, the lower the flexibility and the higher the torquability of the section.

As shown in FIG. 4A, an elongated section 300 includes a plurality of axially extending beams 302 and circumferentially extending rings 304. The elongated section 300 has a two-beam cut pattern because two circumferentially opposing beams 302 are disposed between each pair of adjacent rings 304. The opposing cuts in each cut pair will typically have equal depth, leaving each beam of the resulting beam pair symmetrically circumferentially spaced. Other embodiments may include cut pairs with opposing cuts of differential depth. The greater the difference between the depths of opposing cuts in each cut pair, the closer together circumferentially the beams of the resulting beam pair will be, and therefore the more similar functionally the two-beam cut will be to a one-beam cut.

The illustrated embodiment shows a distribution of beam pairs angularly offset by 90 degrees from one pair to the next along the axis of the member. In alternative embodiments, the angular offset may be more or less than 90 degrees. For example, the angular offset may be about 5, 15, 30, 45, 60, 75, 80, or 85 degrees (in either direction), or may include a plurality of different offset values.

In some embodiments, an angular offset is applied at each successive beam pair. In other embodiments, an angular offset is applied at each successive "segment," with each segment including more than one beam pair. As used herein, a "segment" is a repeating structural unit of the catheter section. In some embodiments, a single segment can be defined as a first pair of opposing beams 302 disposed between two adjacent rings 304 (one proximal ring and one distal ring) and a second pair of opposing beams extending from the distal ring and being rotationally offset by about 90 degrees from the first pair of opposing beams 302. Thus, an embodiment having such segments and having a rotational offset of 5 degrees from segment to segment would have a first beam pair at a 0 degree position, a second at 90 degrees, a third at 5 degrees, a fourth at 95 degrees, etcetera.

FIG. 4B illustrates an elongated section 400 having a plurality of beams 402 and rings 404 arranged in a three-beam configuration. In this embodiment, each triad of beams at each cut location is symmetrically circumferentially spaced by 120 degrees. An angular offset of 60 degrees is applied at each successive cut location. As with the two-beam configuration described above, the beams of a triad need not be symmetrically spaced. Likewise, an angular offset of more or less than 60 degrees may be used, and it may be applied at each successive cut location or at each successive segment. In a three-beam configuration, for example, a segment may be defined as a first triad of beams 402 disposed between two adjacent rings 404 (one proximal ring and one distal ring) and a second triad of beams extending from the distal ring and being rotationally offset by about 60 degrees from the first triad 402.

FIG. 4C illustrates an elongated section 500 having a series of beams 502 and rings 504 arranged in a one-beam configuration. An angular offset of 180 degrees is applied at each successive cut location. As with the other configurations described above, an angular offset of more or less than 180 degrees may be used, and it may be applied at each successive cut location or at each successive segment. In a one-beam configuration, for example, a segment may be defined as a first beam 502 disposed between two adjacent rings 504 (one proximal ring and one distal ring) and a second beam extending from the distal ring and being rotationally offset by about 180 degrees from the first beam 502.

FIG. 4D illustrates another embodiment of an elongated section 600 having a series of beams 602 and rings 604 arranged in a one-beam configuration. In this embodiment, the cuts are provided so that the beams 602 are aligned along one side of the section length, rather than having an angular offset. Such an embodiment can beneficially provide preferential bending in one direction (i.e., toward the aligned beams 602). FIGS. 4C and 4D are examples of one beam configurations where any combination of beams with a rotational offset or a series of beams aligned on one side can be used depending on the balance of performance attributes desired. For example, two beams in succession can be aligned followed by a beam being rotationally offset by some amount (e.g., 180 degrees). Of course, as described elsewhere herein, one beam offsets can be aligned (0 degree offset), or can have a rotational offset of up to 180 degrees, including any angle in between (175 degrees, 135 degrees, 90 degrees, 45 degrees, 5 degrees, etc.).

Figure 5:
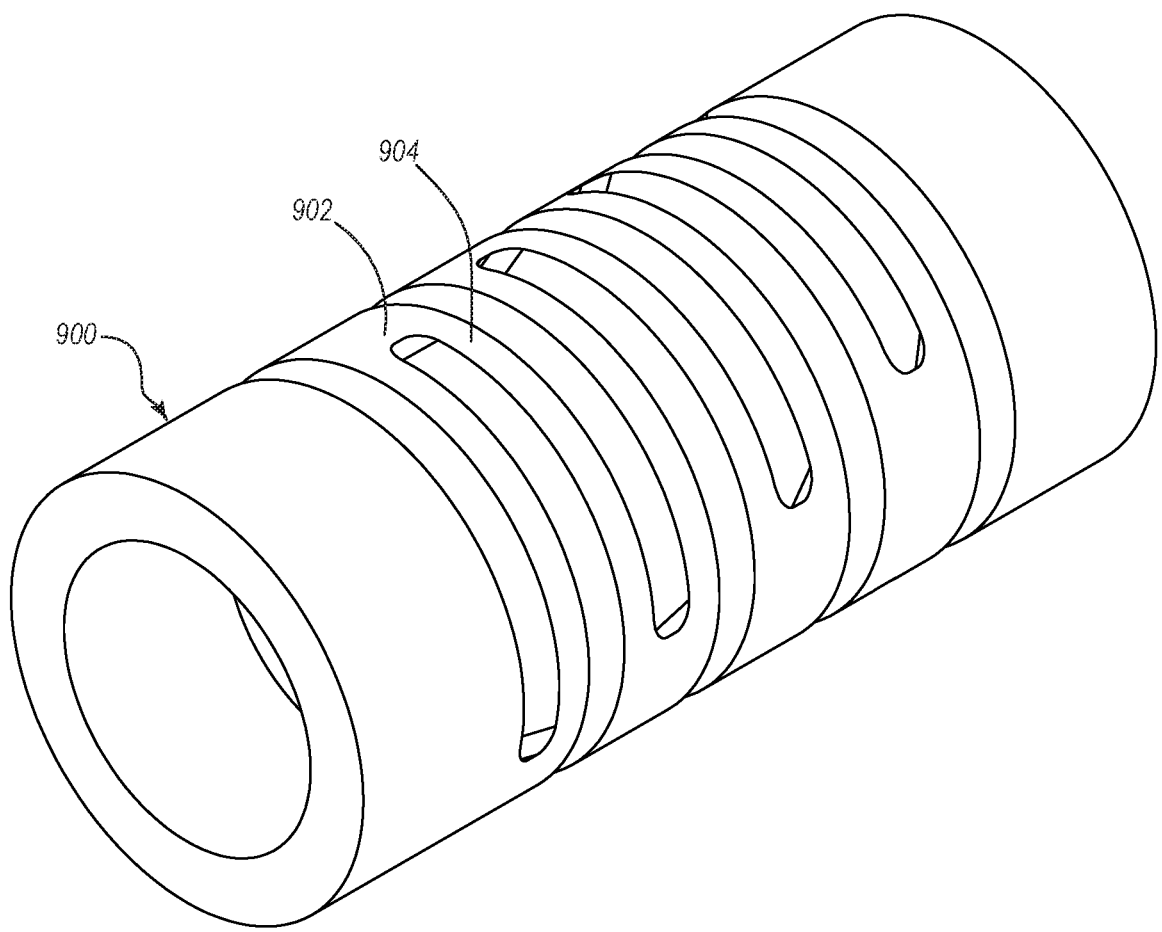
FIG. 5 illustrates a cutting pattern with a helical arrangements of beams.

FIG. 5 illustrates an embodiment of a typical helical cut pattern intended to minimize preferred bending directions. As shown, a rotational offset is applied at each successive segment of the elongate member 900 to form the helical pattern. FIG. 5 illustrates a helical one-beam cut pattern where each cut leaves a single beam 902 between each set of adjacent rings 904. Although successive beams are shown as being offset by about 180 degrees, each successive pair is part of a "segment," and each successive segment is shown as having a rotational offset of about 5 degrees The rotational offset may be applied from segment to segment, as shown in FIG. 5, or may alternatively be applied at each successive cut. This type of helical arrangement may also be used in embodiments having different cut configurations. For example, a two-beam configuration may have a helical arrangement with rotational offset applied at each successive segment or at each successive cut pair.

B. Distributed Patterns

Figure 6:
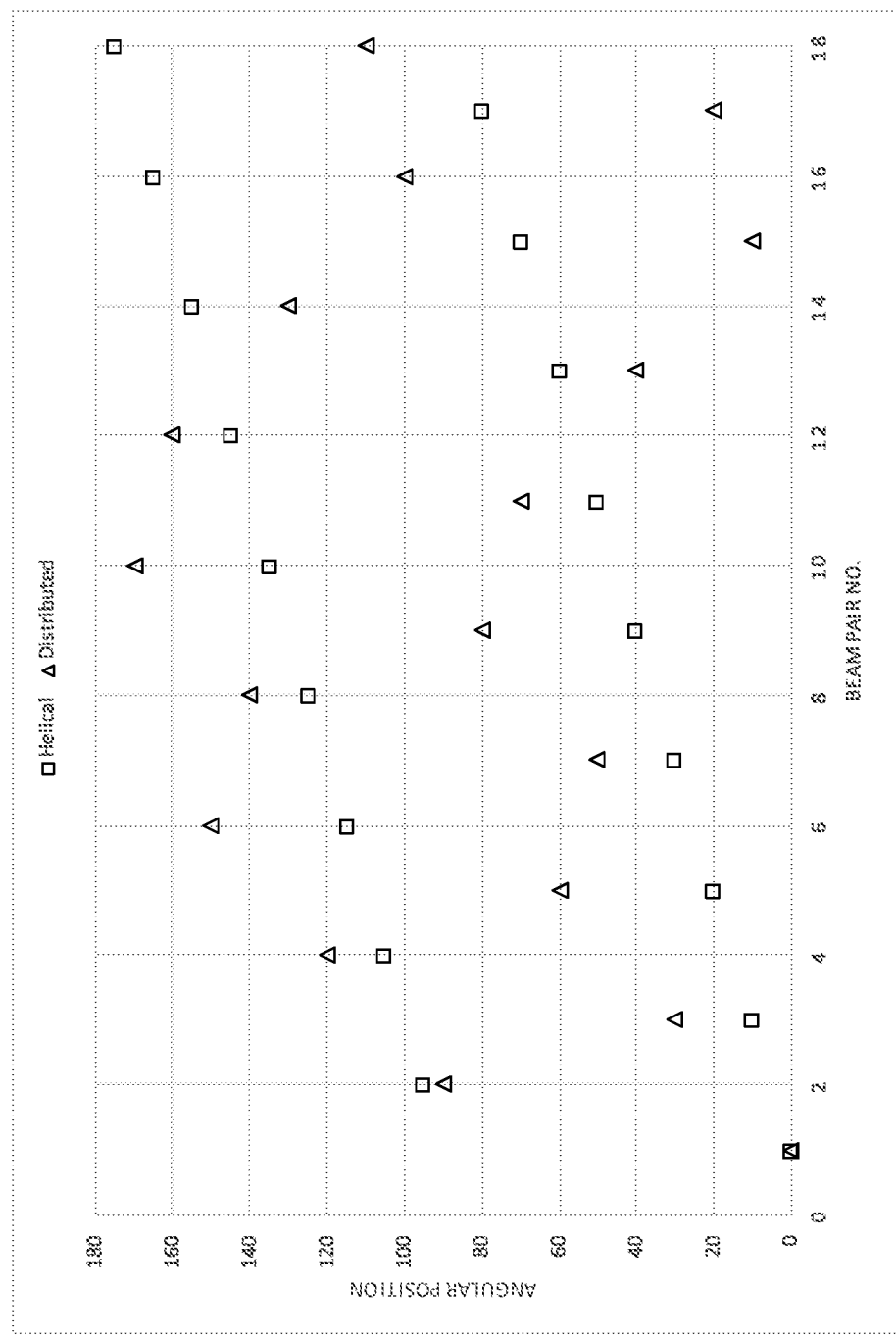
FIG. 6 graphically illustrates a distributed cut pattern and shows a typical helical pattern for comparison.

Some embodiments may include a section having a distributed beam arrangement resulting from a non-helical and non-linear cut pattern. This type of pattern effectively eliminates or minimizes preferred bending directions. FIG. 6 graphically compares one example of a distributed pattern with a conventional helical pattern. As shown, the helical cut pattern applies a constant rotational offset from segment to segment along the length of the elongated member. The distributed cut pattern applies a rotational offset that effectively distributes bending axes without relying on a helical pattern.

The helical and distributed patterns graphically shown in FIG. 6 are for devices having a two-beam configuration. Since a typical two-beam configuration will space each beam pair apart by about 180 degrees, a beam pair at a given position will be indistinguishable from a beam pair rotationally offset by 180 degrees. Accordingly, the possible rotational positions for beam pairs are shown as ranging from 0 to 180 degrees, with the zero and 180 degree positions being equal to one another. Other distributed pattern embodiments may exhibit different rotational spacing. For example, a one-beam configuration will typically be distributed across the full available 360 degree rotational space, and a three-beam pattern will typically exhibit 120 degree symmetry, and therefore be distributed across a 120 degree rotational space.

The distributed pattern shown in FIG. 6 is "non-helical." A helix is commonly defined as following a curve on a conical or cylindrical surface that would become a straight line if the surface were unrolled into a plane. Using the helical cut pattern shown in FIG. 5 as an example, any curved lines tracing the arrangement of the segments along the length of the elongated member 900 would form straight lines if the elongated member 900 were cut open and "unrolled" into a plane. In contrast, in the distributed pattern shown in FIG. 6, there are no lines tracing the arrangement of the beams/segments that form straight lines.

Given a starting beam pair arbitrarily assigned to a zero degree position, successive beam pairs are rotationally offset to maximize the radial distribution of beam positions across the available 180 degree rotational space as quickly as possible (i.e., in as few cuts as possible). However, in the illustrated embodiment, a rotational offset limit is also applied to prevent the formation of rigid spacing artifacts (discussed further below with respect to FIGS. 9 and 10).

The rotational offset limit defines a limit on the acceptable rotational "jump" from one beam pair to the next or from one segment to the next. A rotational offset limit with a value of about 10 to 30 degrees from one segment to the next, or a rotational offset limit that rotates successive beam pairs by 90 degrees±that value, has been shown to provide effective distribution of bending axes without causing overly rigid spacing artifacts. For example, the rotational offset limit may restrict rotation from one beam pair to the next to a value within a range of about 60 to 120 degrees, or about 70 to 110 degrees, or about 80 to 100 degrees. Other embodiments may utilize other rotational offset limits, or may even omit the rotational offset limit, depending on particular product and/or application needs. For example, the rotational offset limit may be raised to a value higher than 30 degrees if the resulting spacing artifacts are acceptable for a particular application.

The exemplary distributed cut pattern illustrated in FIG. 6 utilizes a rotational offset limit of 30 degrees. As shown, a first beam pair is positioned at an arbitrary 0 degree position, and the second beam pair is positioned at 90 degrees. The greatest remaining gaps in the available 180 degree space are between 0 and 90 degrees and between 90 and 180 degrees (where 0 and 180 degrees represent the same position). Placing the next beam pair near a midpoint of one of these gaps, such as at 45 degrees, would best distribute the bending axes of the device. However, placing the next beam pair at 45 degrees would violate the rotational offset limit of 30 degrees. The next beam pair is therefore placed to be close to the midpoint of a remaining gap without violating the rotational offset limit. In this example, the third beam pair is placed at 30 degrees. The fourth beam pair is placed at 120 degrees, which is 90 degrees from the third beam pair.

In this particular example, every other beam pair is offset 90 degrees from the previous beam pair. Alternative embodiments need not necessarily follow this particular pattern. For example, where the illustrated embodiment is an example of varying the applied offset from segment to segment, other embodiments may apply the variable offset from beam pair to beam pair.

Continuing with the example distribution of FIG. 6, the largest remaining positional gaps are now between 30 and 90 degrees and between 120 and 180 degrees. The fifth and sixth beam pairs are placed at 60 and 120 degrees, respectively. The remaining positional gaps are now located every 30 degrees (i.e., between 0 and 30 degrees, between 30 and 60 degrees, between 60 and 90 degrees, etc.). As the pattern continues, remaining angular positions are filled in a manner that radially spaces beam pairs as fast as possible without violating the rotational offset limit.

In the illustrated example, the available angular positions are provided at a granularity of 10 degrees. In other words, all angular positions may be considered as filled when each 10 degree increment has been filled. The illustrated pattern may therefore includes beam pairs positioned at approximately every 10 degree position before resetting. Such an arrangement is referred to herein as having a "positional granularity" of 10 degrees. Alternative embodiments may utilize a different positional granularity, such as a granularity of 0.1, 0.5, 1, 3, 5, 10, 15, 18, 20, 25, or 30 degrees, for example.

The exact positioning illustrated may be adjusted, and it will be understood that the pattern shown in FIG. 6 is illustrative only. For example, the positional gaps may be filled using a different particular sequence as long as rotational jumps are within the predetermined rotational offset limit. Preferably, when filling in gaps between rotational positions, the next beam pair is positioned to be close to the approximate center of the largest remaining positional gap without violating the rotational offset limit. For example, where a gap exists between the 0 degree position and the 30 degree position, the segment may be positioned at the 10 to 20 degree position.

Further, alternative embodiments may utilize a positional granularity that fills in positions of more or less than 10 degrees. Where fewer segments are used before resetting the pattern, the size range of each suitable position will be larger, and where more segments are used before resetting the pattern, the size ranges will become smaller. Some embodiments may include about 6 to 36 beam pairs, or about 10 to 18 beam pairs, before the availability of filled angular positions within the 180 degree radial space is reset. Other embodiments may include many more beam pairs before available positions are reset. As the predetermined positional granularity is lowered, the number of beam pairs needed to fill all available angular positions will rise. Thus, a device having a positional granularity of 1 degree will use 180 beam pairs to fill 180 available angular positions.

Moreover, because there are multiple ways of filling available angular positions according to the predetermined parameters (e.g., positional granularity and rotational offset limit) of the selected distributed pattern, the distributed cut pattern need not identically repeat itself after resetting. Therefore, as used herein, the terms "reset," "resetting," and the like refer to resetting the availability of angular positions within the 180 degree radial space after it has been filled by beam pairs, and the terms do not necessarily imply that the subsequent refilling of angular positions along the next section of the elongated member will exactly repeat the previous pattern. Indeed, in at least some embodiments, the entire length of the distributed pattern may be non-repeating.

It will be understood that the foregoing principles may also be applied to an embodiment having a one-beam arrangement, an embodiment having a three-beam arrangement, or an embodiment having more than a three-beam arrangement. The same principles described above may be applied to a one-beam embodiment, except that the range of angular positions to fill will extend to 360 degrees. Likewise, the same principles may be generally applied to a three-beam embodiment, except that the range of angular positions to fill will typically extend to 120 degrees.

C. Imperfect Ramp Patterns

Figure 7:
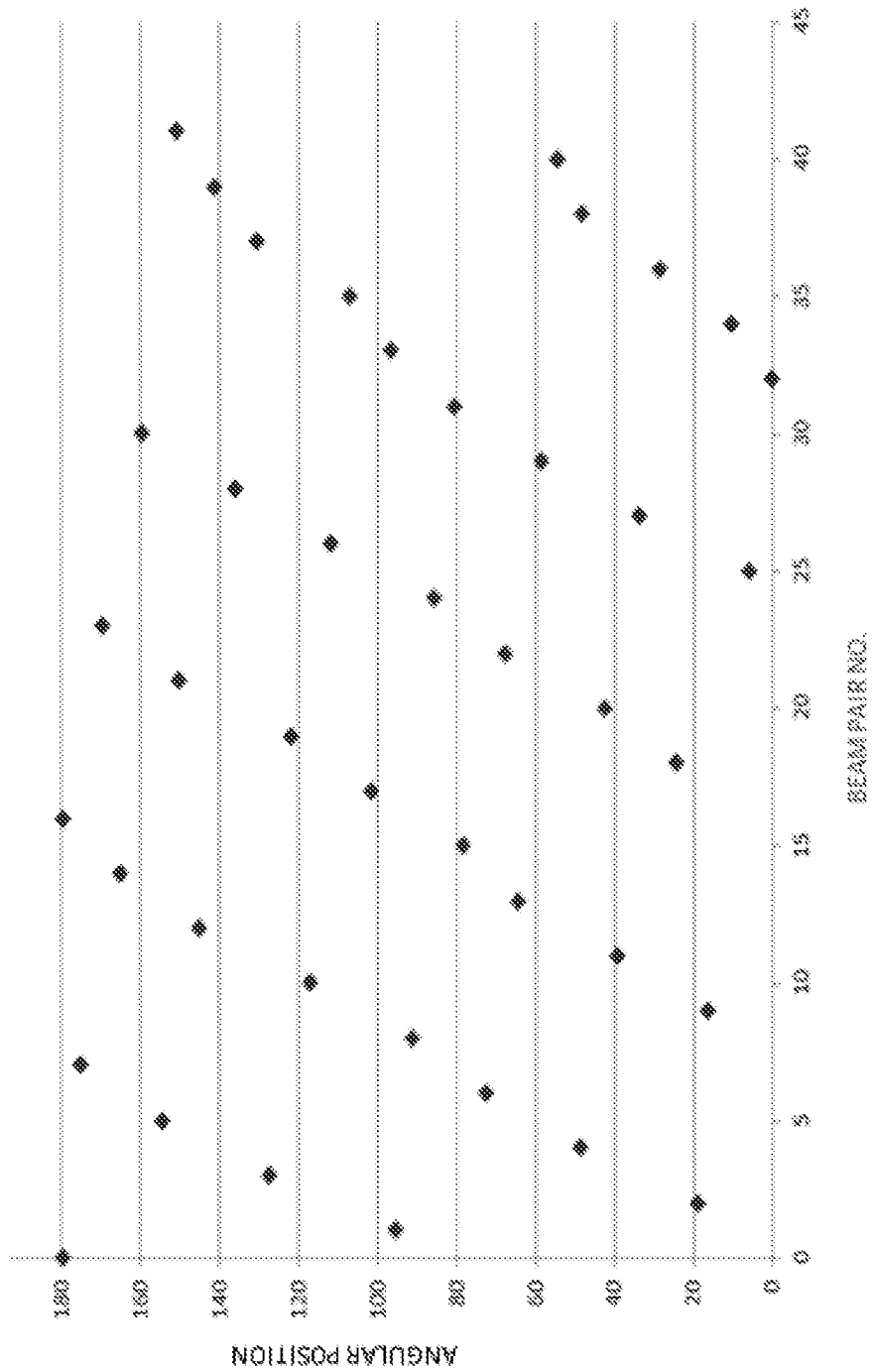
FIG. 7 graphically illustrates an imperfect ramp cut pattern.

FIG. 7 graphically illustrates another embodiment of a non-helical cut pattern formed by intentionally disrupting an otherwise helical pattern with a series of purposefully designed imperfections. This type of cut pattern is referred to herein as an "imperfect ramp" pattern. The intentional divergences of an imperfect ramp pattern beneficially function to reduce or prevent preferred torsional and curvature relics inherent in a true helical arrangement. As shown, segments are arranged such that no three successive beam pairs or segments are spaced according to the same rotational offset. In other words, no three beam pairs or segments are arranged so as to form a straight line if the cylindrical elongated member were unrolled into a plane.

In contrast to the imperfect ramp patterns of FIG. 7, a true helical pattern is typically formed by rotationally offsetting each successive segment or each successive beam pair by a constant value. For example, a true helical pattern in a two-beam structure may be formed by rotationally offsetting each successive cut pair by a constant value of 5 degrees, 85 degrees, 95 degrees, or some other constant value that is not a multiple of 90 degrees.

In an imperfect ramp cut pattern, the modifying value is intentionally made variable rather than constant. For example, as in FIG. 7, an imperfect ramp pattern may be formed by rotationally offsetting each successive beam pair by a constant value ±a variable modifying value. A rotational offset that includes a constant value ±a variable modifying value is referred to herein as an "imperfect rotational offset."

The variable modifying value may range from 5 to 15 degrees. In other embodiments, the variable modifying value may range from 2.5 to 30 degrees, or some other range suitable for the intended purpose of the resulting device. The variable modifying value is preferably randomly selected at each segment or beam pair to which it is applied, with upper and lower bounds of the random selection being defined by the modifying value range (e.g., 5 to 15 degrees). The constant value portion of the offset is typically 180 degrees in a one beam pattern, 90 degrees in a two-beam pattern, 60 degrees in a three-beam pattern, etcetera.

Alternative embodiments may apply the imperfect ramp pattern between segments of different sizes and/or between segments with different internal offsets. For example, some embodiments may include segments having more than two pairs of beams (and more than two corresponding rings) and/or with internal offsets different than 90 degrees. Further, even though the illustrated example shows a two-beam cut pattern where each pair of the opposing cuts results in two circumferentially opposing beams, it will be understood that the distributed offset patterns may also be applied to one-beam cut patterns, three-beam cut patterns, and patterns having more than three beams between adjacent rings.

D. Sawtooth Patterns

Figure 8:
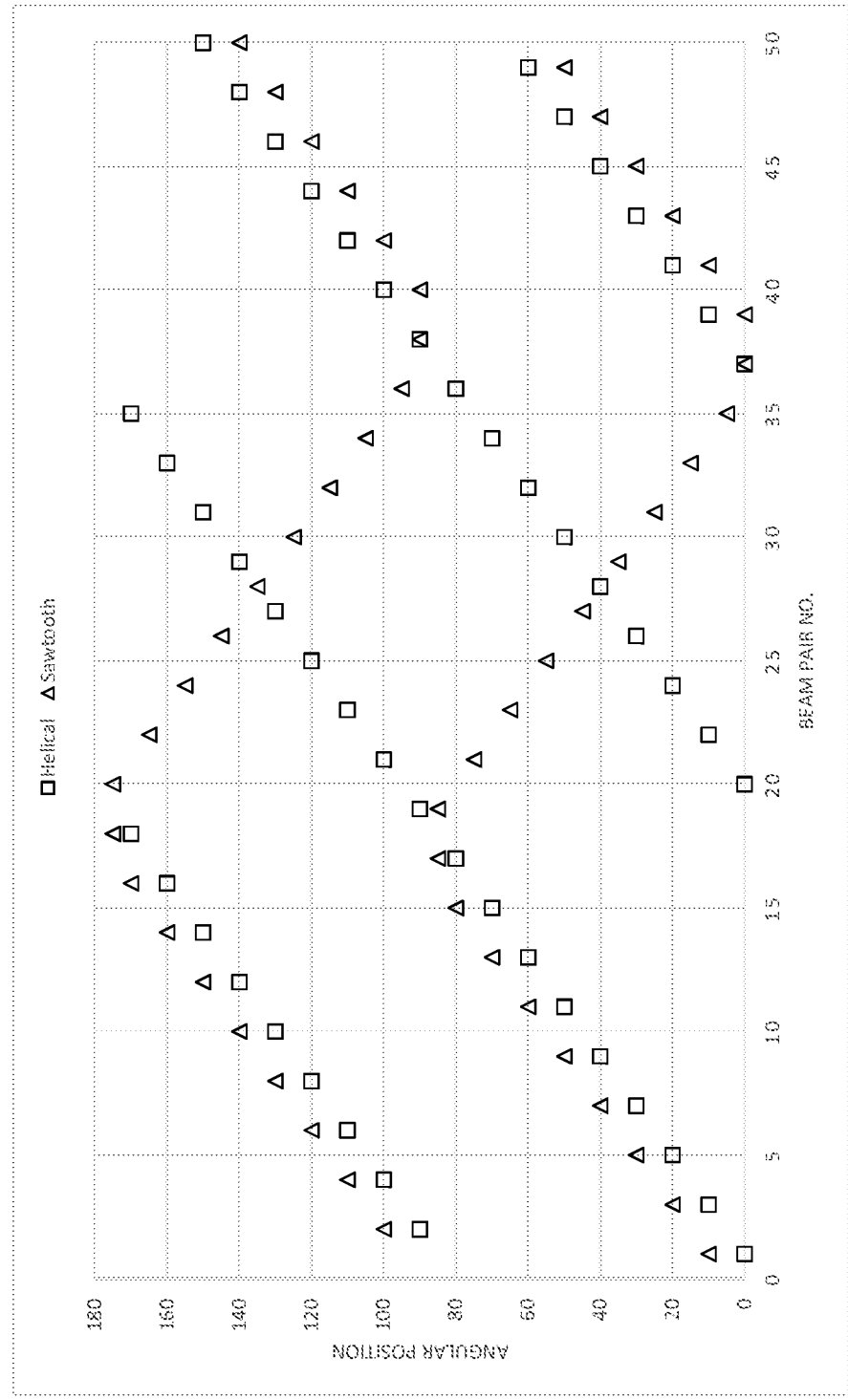
FIG. 8 graphically illustrates a sawtooth cut pattern and shows a typical helical pattern for comparison.

FIG. 8 illustrates another embodiment of a non-helical cut pattern referred to herein as a "sawtooth" pattern. As with other non-helical cut patterns described herein, the sawtooth cut pattern can beneficially avoid preferred bending axes while also limiting preferred curvature directions inherent in helical patterns. In contrast to a helical pattern, a sawtooth cut pattern periodically reverses the direction of the rotational offset.

Both the sawtooth pattern and the helical pattern of FIG. 8 have an angular offset of about 10 degrees between adjacent segments, with each cut pair within each segment offset by 90 degrees. Whereas the helical pattern simply continues with these offset values in the same direction through multiple rotations around the circumference of the elongated member, the sawtooth pattern reaches a first apex position before reversing direction and continuing toward a second apex position. Upon reaching the second apex position, the sawtooth pattern then reverses again and continues back toward the first apex. The pattern then repeats along the desired length of the elongated member.

For example, the first apex position is set at about 90 degrees (i.e., 90 degrees for the first cut pair of the segment and 180 degrees for the second cut pair of the segment). Upon reaching the first apex position, the pattern reverses toward the second apex position. In this embodiment, the second apex position is set at about 0 degrees (i.e., 0 degrees for the first cut pair of the segment and 90 degrees for the second cut pair of the segment). Alternative embodiments may include other apex positions. Given an arbitrary zero degree starting position, the first apex position is less than 360 degrees in a one-beam configuration, less than 180 degrees in a two-beam configuration, less than 120 degrees in a three-beam configuration, and so on. Preferably, the first apex position is about 180 degrees for a one-beam configuration, 90 degrees for a two-beam configuration, 60 degrees for a three-beam configuration, and so on.

As described above, the angular offset from segment to segment in the sawtooth pattern of FIG. 8 is about 10 degrees. In other embodiments of sawtooth cut patterns, the angular offset may be more or less than 10 degrees, such as from about 5 degrees to about 30 degrees. Additionally, or alternatively, portions of the cut pattern between the apexes may include a variable offset. For example, one or more portions between the apexes may include an imperfect rotational offset such as described above in relation to FIG. 7.

Alternative embodiments may apply the sawtooth pattern between segments of different sizes and/or between segments with different internal offsets. For example, some embodiments may include segments having more than two pairs of beams (and more than two corresponding rings) and/or with internal offsets different than 90 degrees. Further, even though the illustrated example shows a two-beam cut pattern where each pair of the opposing cuts results in two circumferentially opposing beams, it will be understood that the distributed offset patterns may also be applied to one-beam cut patterns, three-beam cut patterns, and patterns having more than three beams between adjacent rings.

E. Spacing Artifacts

Figure 9:
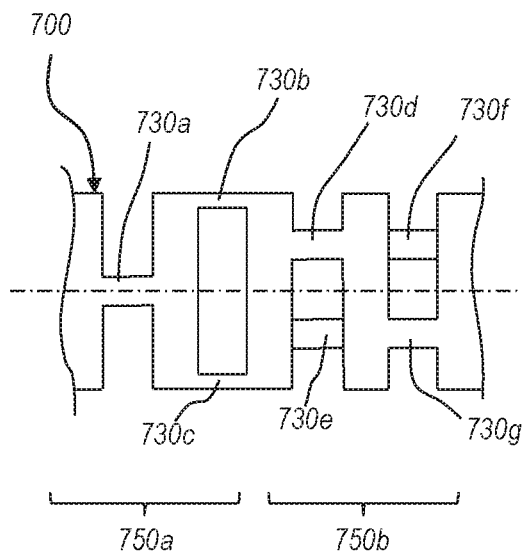
FIGS. 9 and 10 illustrate differences in rotational offsets, showing differences in spacing artifacts resulting from different sizes of rotational offset jumps.

FIG. 9 illustrates an example of an undesirable spacing artifact that may result where a rotational offset limit is not applied. FIG. 9 illustrates a section of an elongated member 700 having a first segment 750a and a second segment 750b. The first segment 750a includes a first pair of beams 730a (only one of which is visible in this view) and second pair of beams 730b and 730c which are offset from the first pair by 90 degrees. The second segment 750b includes a first pair of beams 730d and 730e, and a second pair of beams 730f and 730g which are offset from the first pair by 90 degrees. Each beam within a pair is circumferentially spaced from its corresponding beam by 180 degrees. The second segment 750b is offset from the first segment 750a by 45 degrees, which positions the first pair of beams 730d and 730e off by 45 degrees from the first pair of beams 730a and positions the second pair of beams 730f and 730g off by 45 degrees from the second pair of beams 730b and 730c.

Applying such a 45 degree offset from the first segment 750a to the second segment 750b may at first be considered desirable because it places the bending axes of the second segment 750b in between the bending axes of the first segment 750a. However, the 45 degree jump also results in beam spacing between segments which can leave an overly rigid artifact in a portion of the elongated member 700. In the illustrated member 700, the beam 730d is only spaced from the beam 730b by 45 degrees, whereas the beam 730e is spaced from the beam 730b by 135 degrees. Likewise, the beam 730e is only spaced from the beam 730c by 45 degrees, whereas the beam 730d is spaced from the beam 730c by 135 degrees. This disproportionate spacing may be undesirable because the region of the elongated member 700 having the smaller spacing may be overly rigid and/or the region having the larger spacing may be overly flexible.

Figure 10:
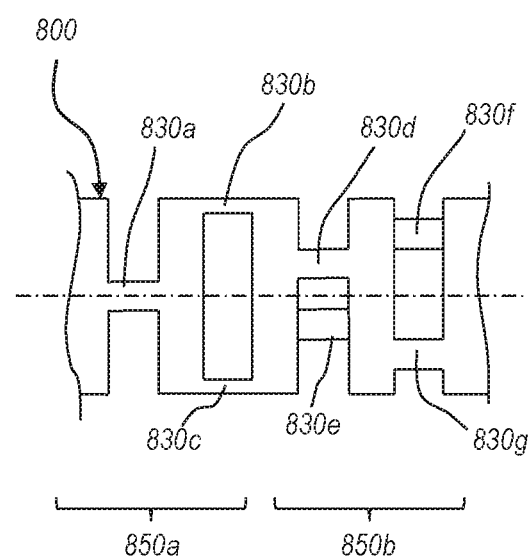

In contrast, a more limited jump in the rotational offset applied from one segment to the next will minimize the discrepancy in beam spacing between segments. For example, FIG. 10 illustrates a section of an elongated member 800 with a more limited rotational offset of about 20 degrees applied between a first segment 850a and a second segment 850b. As in the elongated member 700 of FIG. 9, the first segment 850a includes a first pair of beams 830a and a second pair of beams 830b and 830c, and the second segment 850b includes a first pair of beams 830d and 830e and a second pair of beams 830f and 830g. However, because the second segment 850b is offset from the first segment 850a by a more limited 20 degrees, the spacing discrepancy between beams 830b, 830c, 830d, and 830e is less pronounced. Beam 830d is spaced 70 degrees from beam 830b, and beam 830e is spaced 110 degrees from beam 830b. Likewise, beam 830e is spaced 70 degrees from beam 830c and beam 830d is spaced 110 degrees from beam 830c. Thus, although a spacing discrepancy still exists between segments, it may be controlled to a suitable degree by providing an appropriate rotational offset limit.

F. Spiral Patterns

Figure 11A:
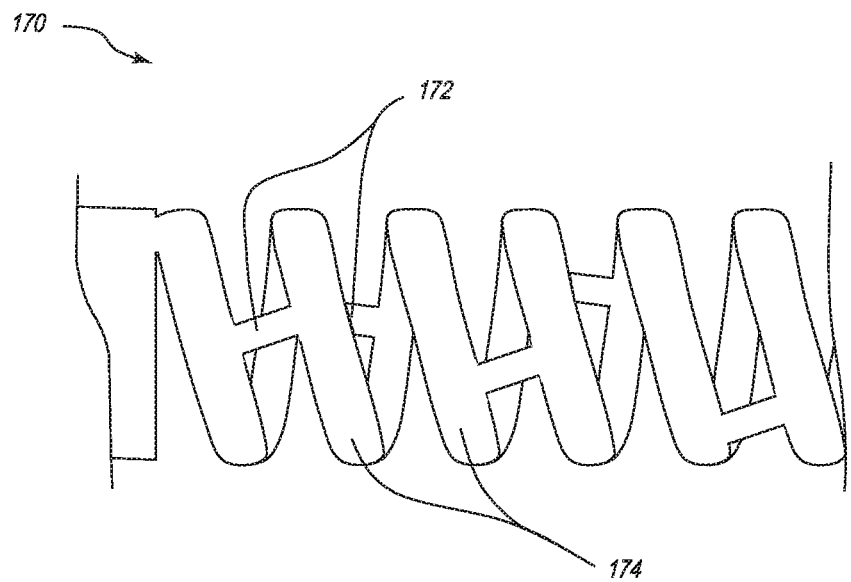
FIGS. 11A through 11C illustrate various spiral cut patterns that may be utilized to provide desired bending characteristics in the distal section of the intravascular device.
Figure 11B:
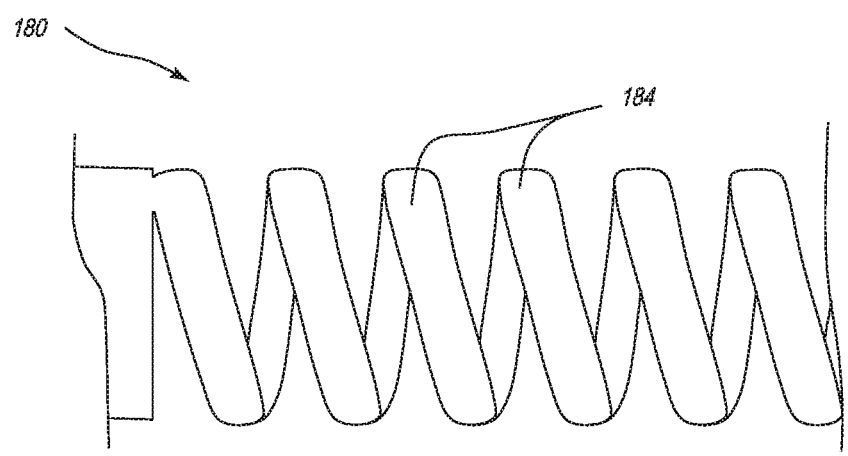
Figure 11C:
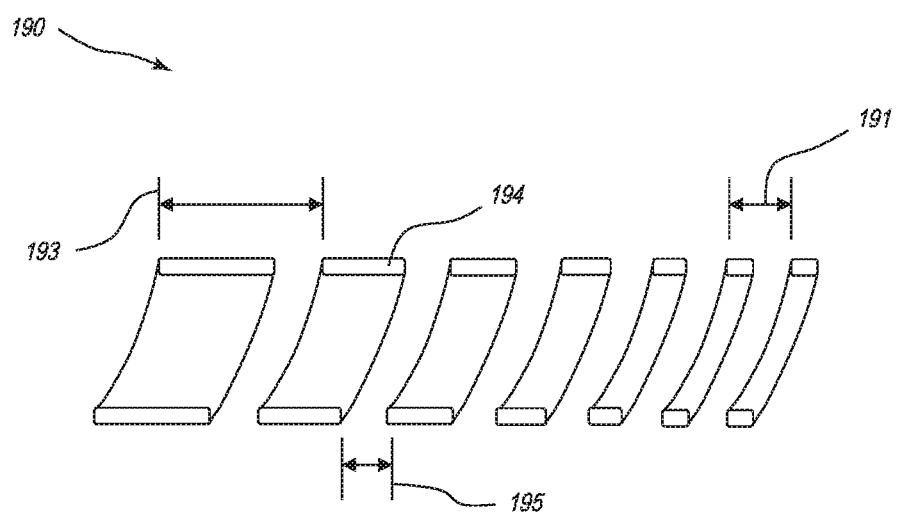

FIGS. 11A through 11C illustrate embodiments of a "spiral" cut pattern that may be included in one or more sections of the device. As shown in FIG. 11A, a section 170 of device is cut to provide an outer body of resulting helically oriented coil members 174, with the pitch of the resulting coil defining the size of the fenestrations. Typically, a spiral cut pattern provides less torquability and more flexibility than a one-beam pattern. As such, in most applications, spiral sections are less beneficial at more proximal sections of the device where torquability concerns are particularly important, but are beneficial at more distal sections, and particularly at or near the distal end of the device, where flexibility concerns become more important.

In preferred embodiments, the spiral cut section 170 forms an integral piece of material with one or more adjacent sections of the elongated device. For example, rather than welding, adhering, or otherwise attaching a separate coil member to another section of the device (which unfavorably introduces potential failure points and increases manufacturing difficulty), the spiral pattern results from a cutting operation performed on the section. In this manner, a single piece of material can be microfabricated to include one or more sections of different cut arrangements, in addition to the one or more spiral cut patterns.

The embodiment shown in FIG. 11A also includes a series of bridges 172 that remain between and connect adjacent coil members 174 of the spiral pattern. Such bridges 172 can function to somewhat limit the flexibility of the section 170 relative to a similar spiral pattern omitting such bridges. FIG. 11B, for example, illustrates another spiral cut section 180 that may be included in the hollow elongated member 104. The spiral cut pattern of section 180 omits bridges between coil members 184, and therefore has relatively greater flexibility than the spiral section 170 shown in FIG. 11A (assuming materials, pitch, diameter, wall thickness, and other relevant factors are otherwise substantially equal). Bridges 172 can also be arranged to provide flexibility bias in one or more directions.

In embodiments having bridges 172, such as the embodiment shown in FIG. 11A, the bridges 172 may be spaced about every 45, 60, 75, 90, 105, 120, 135, 150, 165, or 180 degrees around the spiral shape of the device. Greater spacing may also be provided between successive bridges. For example, multiples of 360 degrees may be added to any of the foregoing angle spacing values to provide an even greater spacing arrangement. Less spacing generally limits flexibility to a greater degree, while greater spacing generally provides greater relative flexibility. In some embodiments, one or more of the bridges 172 may be aligned with the longitudinal axis. Additional or alternative bridges may be oriented at an angle relative to the longitudinal axis. Further, one or more of the bridges 172 may be straight, while additional or alternative bridges may include bends or curved sections, or may include a non-uniform cross-sectional area. The bridges 172 may therefore be modified to adjust the bending, torsional, or axial stiffness of the part as desired. In some embodiments, spacing of the bridges 172 can vary across the length of the section 170. For example, spacing between the bridges 172 can become progressively greater toward the distal end of the section in order to progressively increase distal flexibility.

Additionally, or alternatively, a spiral cut pattern may be varied along its length to provide desired flexibility characteristics. FIG. 11C illustrates, in cross-sectional view, an embodiment of a section 190 where spacing between spiral cuts is tailored to be progressively narrower as the cuts near the distal end of the section. As shown, the dimension 191 between two of the coil members 194 is smaller at a more distal region than the dimension 193 between more proximally located coil members 192. In the illustrated embodiment, the cut width, indicated by dimension 195, is substantially constant. In alternative embodiments, the cut width 195 may be adjusted as an alternative to or in addition to the progressive changes in coil member size shown by dimensions 191 and 193. Other embodiments may omit progressively changing features, or may include one or more sections including progressively changing features and one or more other sections with substantially constant coil dimensionality.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Separate features and components of any embodiment described herein may be combined with features and components of any other embodiment. For example, any combination of the different microfabricated cut patterns described herein may be utilized in the microfabricated sections of the exemplary catheter device of FIG. 3.

The invention claimed is:

1. An interventional device configured for passage to the aortic root and to a coronary artery, the interventional device comprising:
 an elongated member extending between a proximal end and a distal end, the elongated member including:
  a proximal section including a microfabricated region and a braided region proximal of the microfabricated region, the microfabricated region of the proximal section having a cut arrangement for increasing flexibility of the proximal section;
a distal section including a microfabricated region having a cut arrangement for increasing flexibility of the distal section, and wherein the microfabricated region of the distal section has greater flexibility than the microfabricated region of the proximal section; and
an intermediate section between the proximal section and the distal section, the intermediate section having a proximal-intermediate section extending distally from the proximal section and a distal-intermediate section extending proximally from the distal section,
wherein the proximal-intermediate section includes a microfabricated cut arrangement with cuts arranged on a single side to leave a resulting spine and to enable preferential flexing in one plane, and
wherein the distal-intermediate section is more rigid than each of the proximal-intermediate section, the microfabricated region of the proximal section, and the distal section.

2. The device of claim 1, wherein at least the distal section and intermediate section are formed from a single integral piece of stock material.

3. The device of claim 1, wherein at least the distal section, the intermediate section, and a region of the proximal section are formed from a single integral piece of stock material, the region of the proximal section extending proximally from the intermediate section.

4. The device of claim 1, wherein longitudinal spacing between cuts of the microfabricated region of the proximal section grows progressively narrower toward the intermediate section.

5. The device of claim 1, further comprising an outer laminate.

6. The device of claim 5, wherein the outer laminate extends distally beyond the distal section to form an atraumatic distal tip.

7. The device of claim 1, further comprising an inner liner.

8. The device of claim 7, wherein the inner liner extends distally beyond the distal section to form an atraumatic distal tip.

9. The device of claim 1, wherein the distal-intermediate section omits cuts.

10. The device of claim 1, wherein cuts of the microfabricated region of the proximal section are arranged on multiple sides of the proximal section.

11. The device of claim 1, wherein cuts of the microfabricated region of the distal section are arranged on multiple sides of the distal section.

12. A method of accessing a targeted vessel via the aortic root, the method comprising:
providing an interventional device comprising:
an elongated member extending between a proximal end and a distal end, the elongated member including a proximal section having a microfabricated region with a first cut arrangement with cuts arranged on multiple sides, a distal section having a microfabricated region with a second cut arrangement with cuts arranged on multiple sides and that provides greater flexibility than the first cut arrangement, and
an intermediate section between the proximal section and the distal section and that has a proximal-intermediate section extending distally from the proximal section and a distal-intermediate section extending proximally from the distal section,
wherein the proximal-intermediate section includes a microfabricated cut arrangement with cuts arranged on a single side to leave a resulting spine and to enable preferential flexing in one plane, and
wherein the distal-intermediate section omits microfabricated cuts and is more rigid than the proximal-intermediate section and the distal section;
routing the distal end of the interventional device to the aortic root; and
positioning the device such that the proximal-intermediate section abuts an aortic wall at a contact point and forms a bend, and such that the distal-intermediate section extends across the aortic root away from the contact point and towards a targeted vessel to enable the distal section entry into the targeted vessel.

13. The method of claim 12, wherein the targeted vessel is a coronary artery.

14. The method of claim 12, wherein the distal-intermediate section of the interventional device is more rigid than the microfabricated region of the proximal section.

15. The method of claim 12, wherein the proximal section of the interventional device further comprises a braided region.

16. The method of claim 15, wherein the braided region of the proximal section is proximal of the microfabricated region of the proximal section.

17. The method of claim 12, wherein at least the distal section and intermediate section of the interventional device are formed from a single integral piece of stock material.

18. The method of claim 12, wherein longitudinal spacing between cuts of the microfabricated region of the proximal section grows progressively narrower toward the intermediate section.

19. The method of claim 12, further comprising an outer laminate and/or inner liner.

20. The method of claim 19, wherein the outer laminate and/or inner liner extends distally beyond the distal section to form an atraumatic distal tip.

* * * * *